United States Patent
Gupta et al.

(10) Patent No.: US 12,091,706 B2
(45) Date of Patent: Sep. 17, 2024

(54) SEQUENTIAL STAINING FOR MULTIPLEX ANALYSES OF TISSUES AND CELLS

(71) Applicant: Rush University Medical Center, Chicago, IL (US)

(72) Inventors: Vineet Gupta, Chicago, IL (US); Anugraha Rajagopalan, Chicago, IL (US)

(73) Assignee: RUSH UNIVERSITY MEDICAL CENTER, Chicago, IL (US)

(*) Notice: Subject to any disclaimer, the term of this patent is extended or adjusted under 35 U.S.C. 154(b) by 514 days.

(21) Appl. No.: 16/965,368

(22) PCT Filed: Jan. 29, 2019

(86) PCT No.: PCT/US2019/015630
§ 371 (c)(1),
(2) Date: Jul. 28, 2020

(87) PCT Pub. No.: WO2019/152391
PCT Pub. Date: Aug. 8, 2019

(65) Prior Publication Data
US 2021/0230676 A1    Jul. 29, 2021

Related U.S. Application Data

(60) Provisional application No. 62/623,866, filed on Jan. 30, 2018.

(51) Int. Cl.
| | | |
|---|---|---|
| C12Q 1/68 | (2018.01) | |
| C07H 21/00 | (2006.01) | |
| C12Q 1/6806 | (2018.01) | |
| C12Q 1/6818 | (2018.01) | |

(52) U.S. Cl.
CPC .......... *C12Q 1/6818* (2013.01); *C07H 21/00* (2013.01); *C12Q 1/6806* (2013.01)

(58) Field of Classification Search
CPC ............... C12Q 1/6818; C12Q 1/6806; C12Q 1/6804; C12Q 2565/20; C07H 21/00; G01N 33/532
See application file for complete search history.

(56) References Cited

U.S. PATENT DOCUMENTS

| | | |
|---|---|---|
| 8,309,306 B2 | 11/2012 | Nolan et al. |
| 10,197,561 B2 | 2/2019 | Dose et al. |
| 2002/0119456 A1 | 8/2002 | Ness et al. |
| 2010/0151472 A1 | 6/2010 | Nolan et al. |
| 2012/0258881 A1 | 10/2012 | Schwartz et al. |
| 2015/0005188 A1 | 1/2015 | Levner et al. |
| 2015/0368697 A1 | 12/2015 | Samusik et al. |
| 2017/0107563 A1 | 4/2017 | Samusik et al. |

FOREIGN PATENT DOCUMENTS

| | | |
|---|---|---|
| CN | 105738612 A | 7/2016 |
| CN | 106574301 A | 4/2017 |
| EP | 3037820 A1 | 6/2016 |
| JP | 2008241316 A | 10/2008 |
| JP | 2016136937 A | 8/2016 |
| WO | 2015200139 A1 | 12/2015 |
| WO | 2017024298 A1 | 2/2017 |

OTHER PUBLICATIONS

International Search Report, issued in PCT/US2019/015630, dated Jul. 9, 2019.
International Preliminary Report On Patentability, issued in PCT/US2019/015630, dated Aug. 4, 2020.
Didenko, DNA Probes Using Fluorescence Resonance Energy Transfer (FRET): Designs and Applications, BioTechniques, vol. 31, (2001), pp. 1106-1121.
Agasti et al., DNA barcoded labeling probes for highly multiplexed Exchange-PAINT imaging, Chem. Sci., 8, 3080, 2017.
Baker, M. J., Trevisan, J., Bassan, P., Bhargava, R., Butler, H. J., Dorling, K. M., Martin, F. L. (2014). Using Fourier transform IR spectroscopy to analyze biological materials. Nature protocols, 9(8), 1771-1791. https://doi.org/10.1038/nprot.2014.110.
Battich et al, Image-based transcriptomics in thousands of single human cells at single-molecule resolution, Nature Methods, 10, 1127, 2013.
Carstens et al, Spatial computation of intratumoral T cells correlates with survival of patients with pancreatic cancer, Nature Comm., 2017.
Chakraborty, K., Leung, K., Krishnan, Y. "High lumenal chloride in the lysosome is critical for lysosome function." eLife, Jun. 2017, e28862. PMID: 28742019.
Collins et al., A branched DNA signal amplification assay for quantification of nucleic acid targets below 100 molecules/mL, Nucleic Acids Res., 25, 2979, 1997.
Edman et al, Electric field directed nucleic acid hybridization on microchips, Nucleic Acids Research, 25, 4907, 1997.
Kwak, J. T., Hewitt, S. M., Kajdacsy-Balla, A. A., Sinha, S., & Bhargava, R. (2016). Automated prostate tissue referencing for cancer detection and diagnosis. BMC bioinformatics, 17(1), [227]. https://doi.org/10.1186/s12859-016-1086-6.
Modi, S.; Swetha, M.G.; Goswami, D.; Gupta, G.D.; Mayor, S.; Krishnan, Y. "A DNA nanomachine that maps spatial and temporal pH changes in living cells." Nature Nanotechnology, Apr. 2009, 325-330. PMID: 19421220.
Remark et al., In-depth tissue profiling using multiplexed immunohistochemical consecutive staining on single slide, Science Immunology, 2016.
Saha, S., Prakash, V., Halder, S., Chakraborty, K., Krishnan, Y. "A pH-insensitive DNA nanodevice quantifies chloride in organelles of living cells." Nature Nanotechnology, Oct. 2015, 645-651. PMID: 26098226.

(Continued)

Primary Examiner — Jezia Riley
(74) Attorney, Agent, or Firm — Barnes & Thornburg LLP

(57) ABSTRACT

Compositions and methods are provided including a plurality of analyte detection agents, each analyte detection agent includes a labile tag operatively coupled to the analyte detection agent, each labile tag includes a signal that is different from each other labile tag and each analyte detection agent targeting a different analyte.

10 Claims, 37 Drawing Sheets
Specification includes a Sequence Listing.

(56) References Cited

OTHER PUBLICATIONS

Schnitzbauer et al., Super-resolution microscopy with DNA-PAINT, Nature Protocols, 12, 1198, 2017.
Sinnamon et al., RNA detection in situ with FISH-STICs, RNA, 20, 260, 2013.
Sosnowski et al, Rapid determination of single base mismatch mutations in DNA hybrids by direct electric field control, PNAS, 94, 1119, 1997.
Su et al., Kinetics of heterogeneous hybridization on indium tin oxide surfaces with and without an applied potential. Electrophoresis, No. 10, 1551-1557, May 2002.

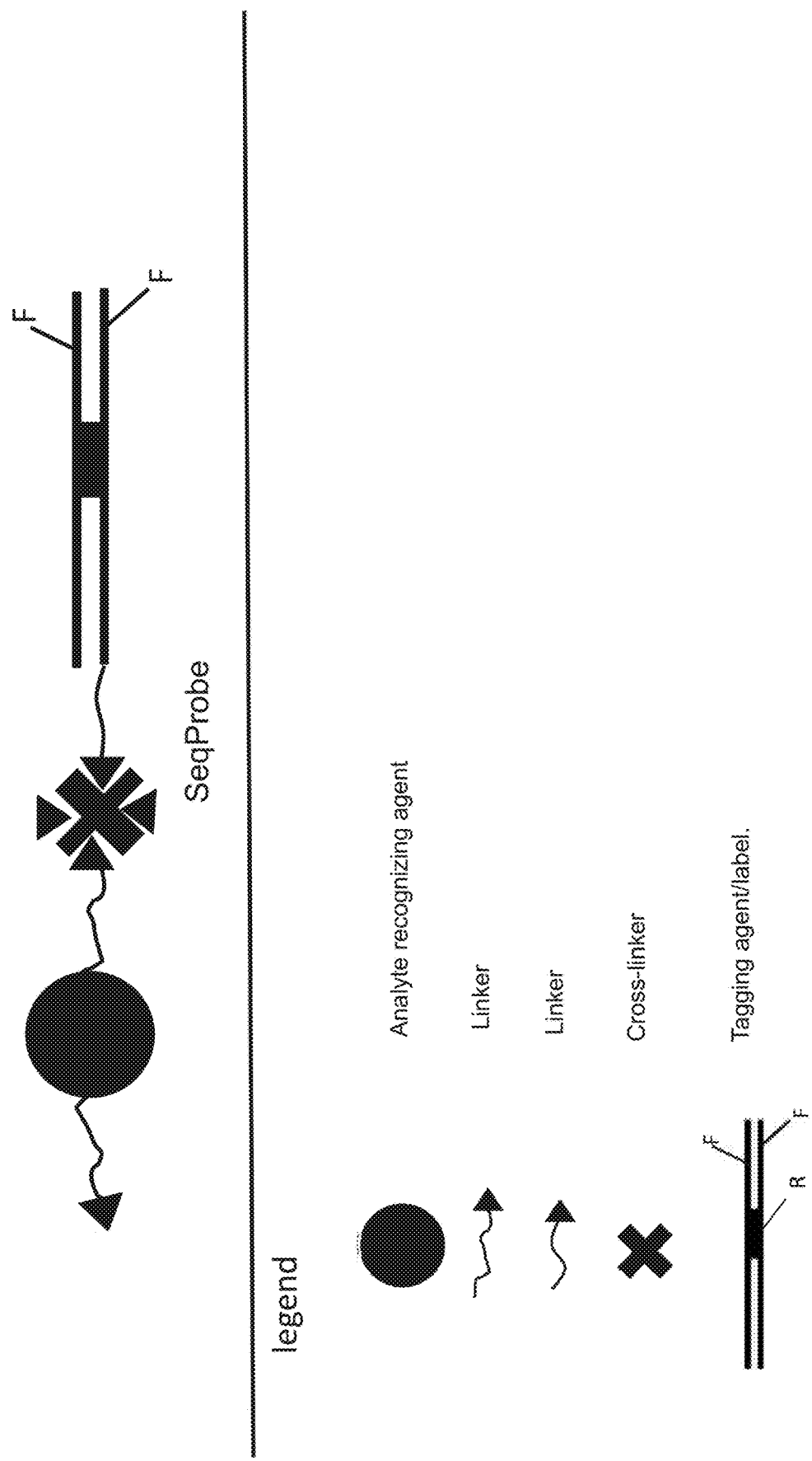

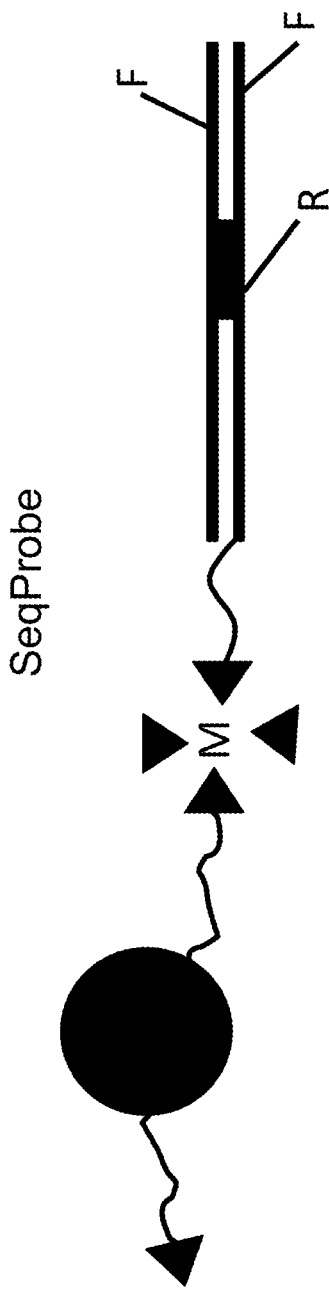
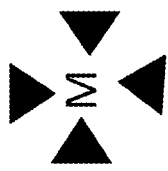
FIG. 2

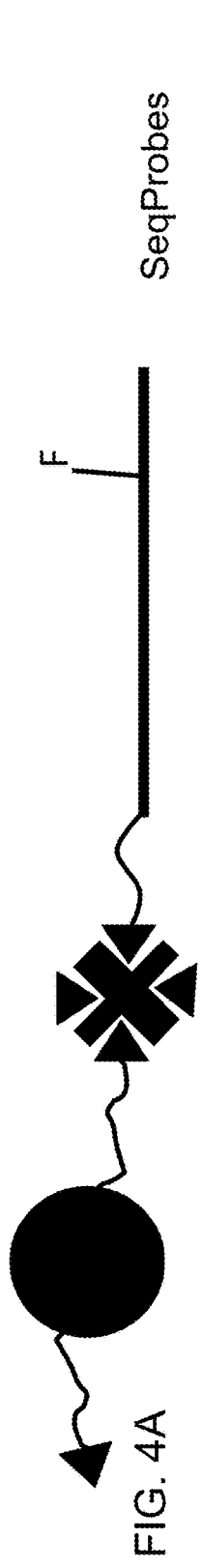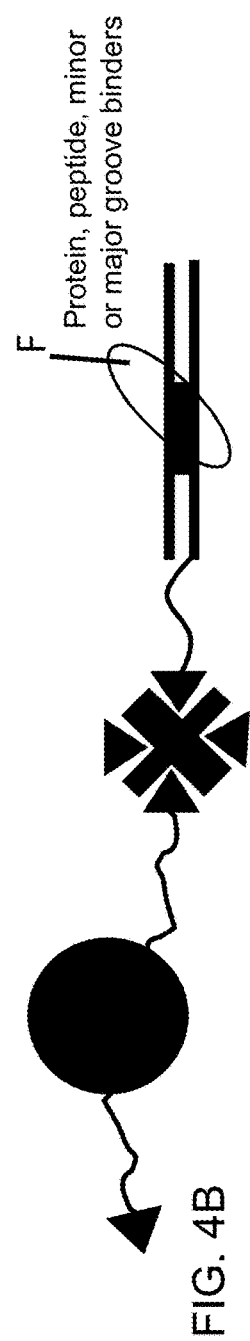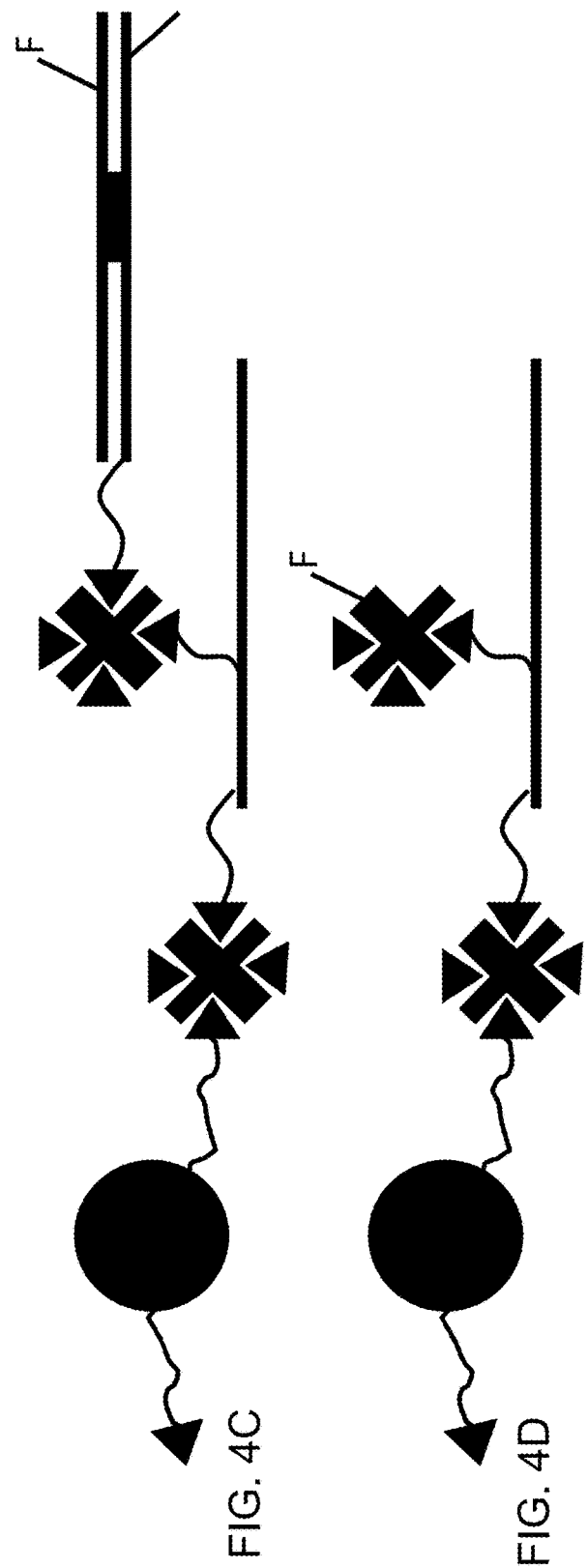
FIG. 4A
FIG. 4B
FIG. 4C
FIG. 4D

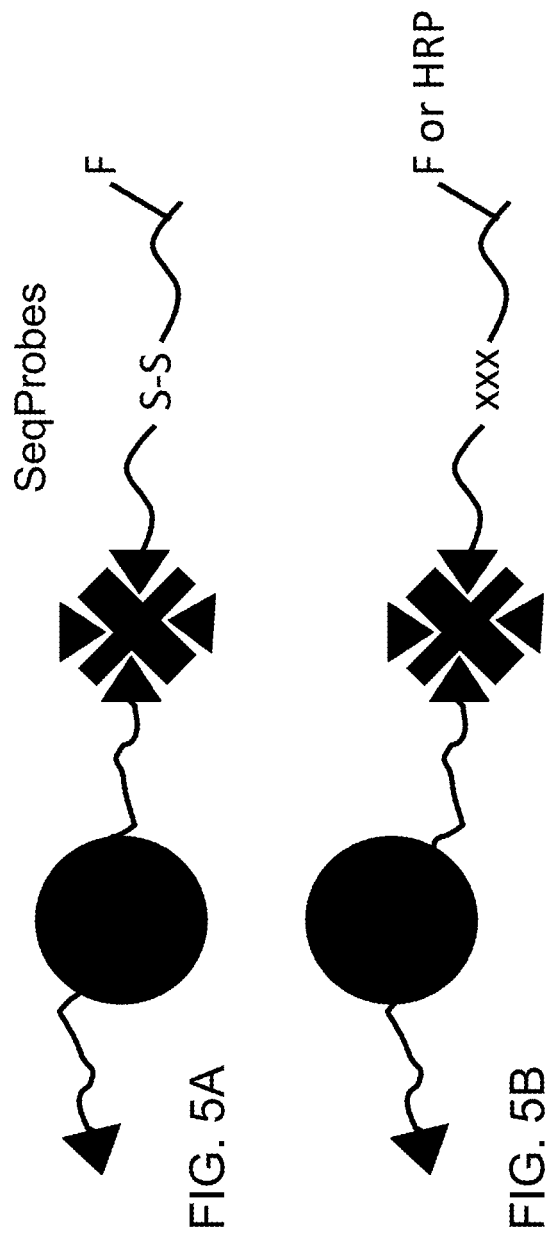

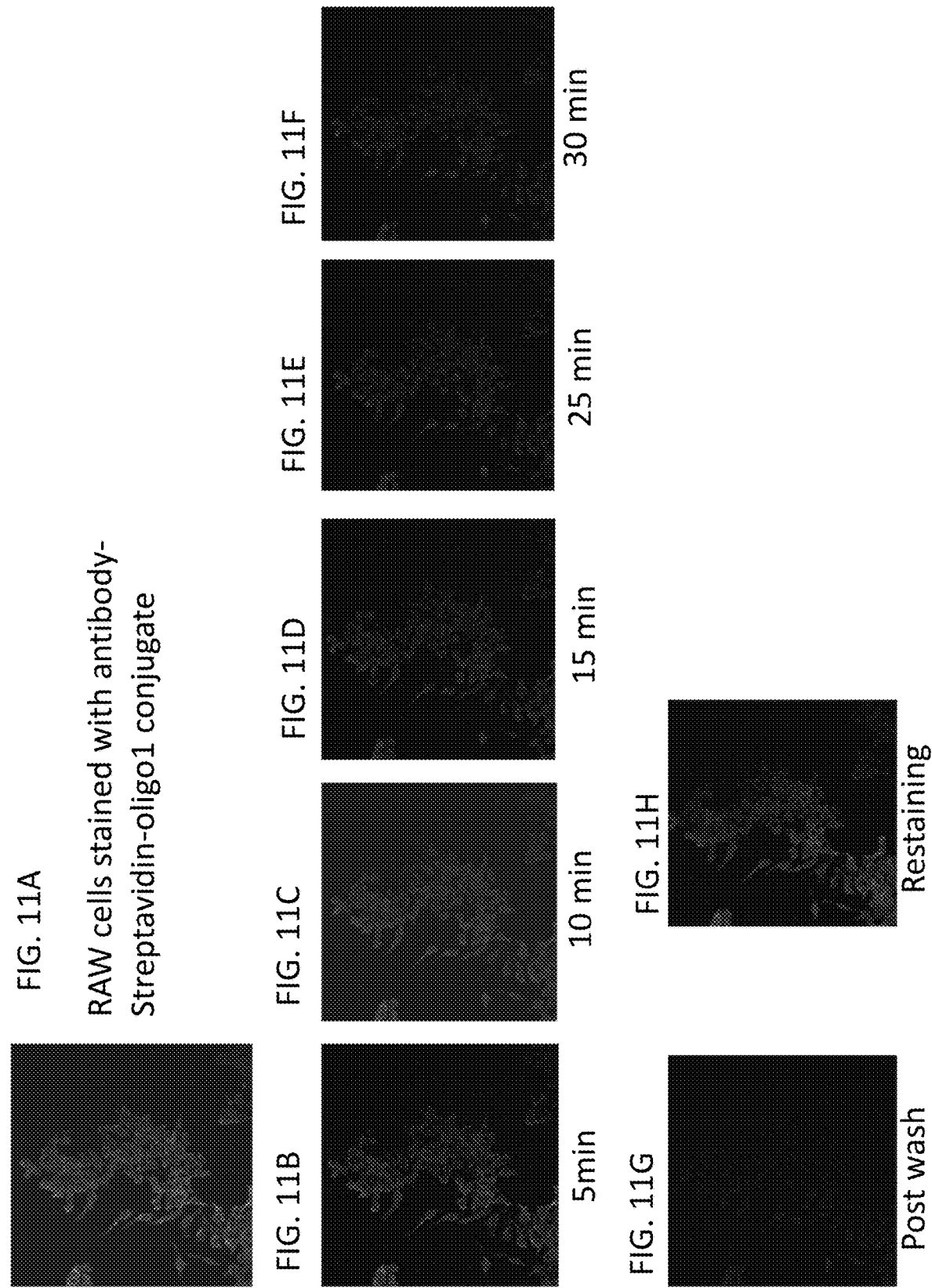

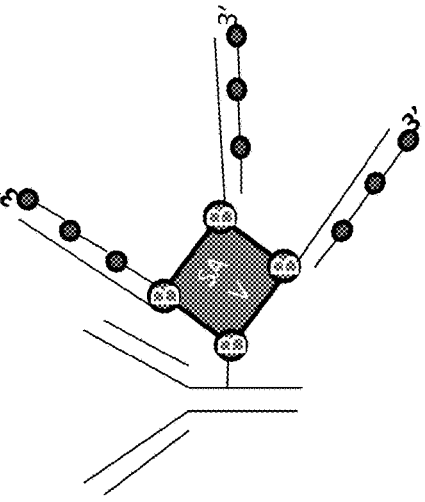
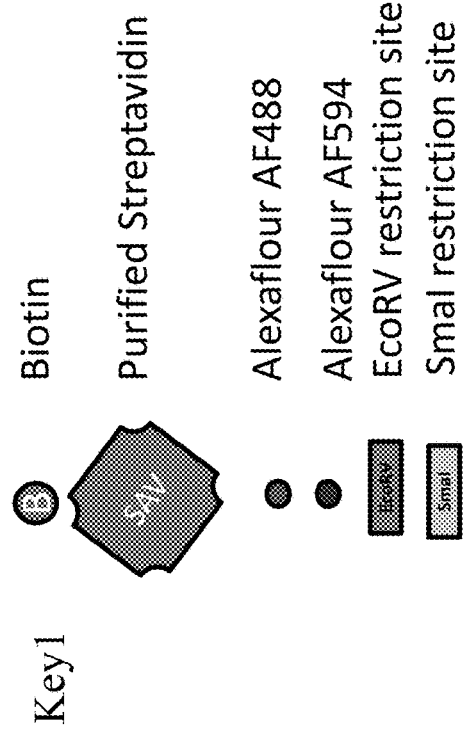
FIG. 12A
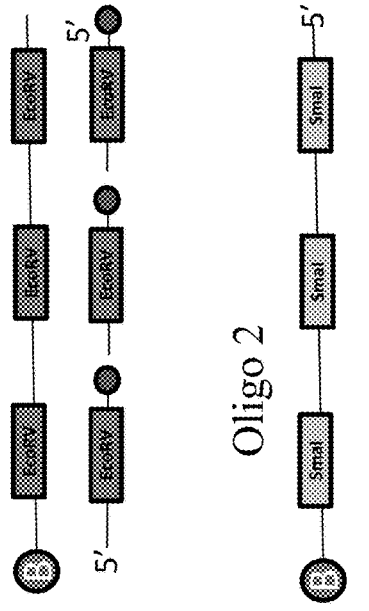
FIG. 12B  Seq1: ATCTGATATCCCGT- AF488
Seq2: GTAGCCCGGGTATG – AF594

Stem Sequence
5'- CGG CAT AGC AGC CCG CAT AC – (TCC ACG GCC CTA GGG ACA ACG)$_{14}$ -3' (SEQ ID NO: 1)

Sequence of Branch oligonucleotides

Oligo A: 5'-xTTxTTxTTxTTxTTxTTxTTxTTxTTxTT TTT TTT TTT TTT- CGT TGT CCC TAG GGC CGT GGA-3' (SEQ ID NO: 2)
Oligo B: 5'-xTTxTTxTTxTTxTTxTTxTTxTTxTTxTT TTT TTT TTT TTT- CGT TGT CGC TAG AGC CGT GGA-3' (SEQ ID NO: 3)
Where x= modified nucleotide, such as 5 me dC (for hydroxy side chain) and an amino-modified nucleotide (for amine side chain)

Each of the "x" sites can be further modified with the following oligo sequence:

Oligo C: ACGGGA TAT CAG AT TTT ACGGGA TAT CAG AT TTT  ACGGGA TAT CAG AT (SEQ ID NO: 4)
Oligo D: ACGGGA TAT CAG AT TTT ACGGGA TAT CAG AT TTT  ACGGGA TAT CAG AT (SEQ ID NO: 5)

Labeled probe sequences:
Seq1 :   ATCTGATATCCCGT- AF488 (SEQ ID NO: 6)
Seq2 :   GTAGCCCGGGTATG – AF594 (SEQ ID NO: 7)

Linker oligo sequences
5'- ACGGGATATCAGATACGGGATATCAGATACGGGATATCAGAT – 3' Biotin (SEQ ID NO: 8)

FIG. 14     Branched DNA design

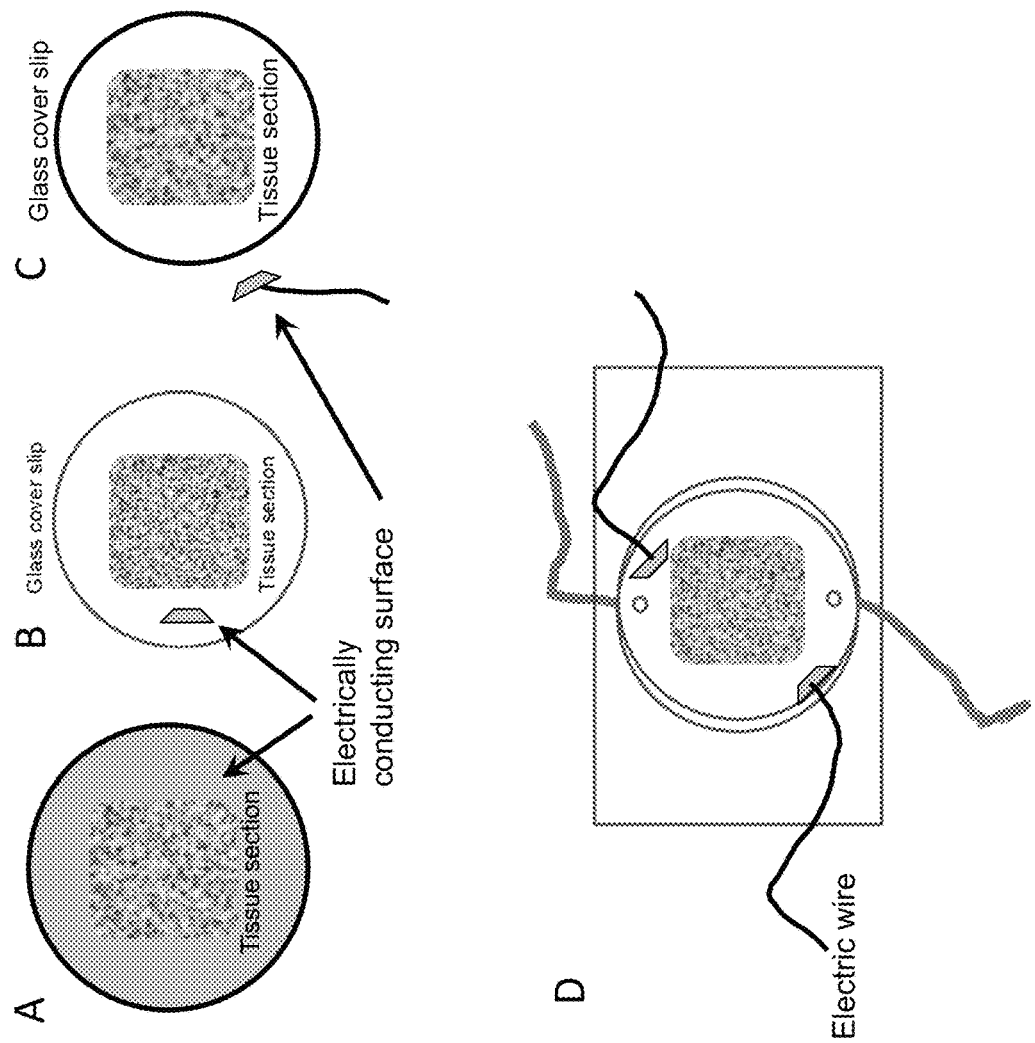
FIG. 15 Use of electric field and/or heaters

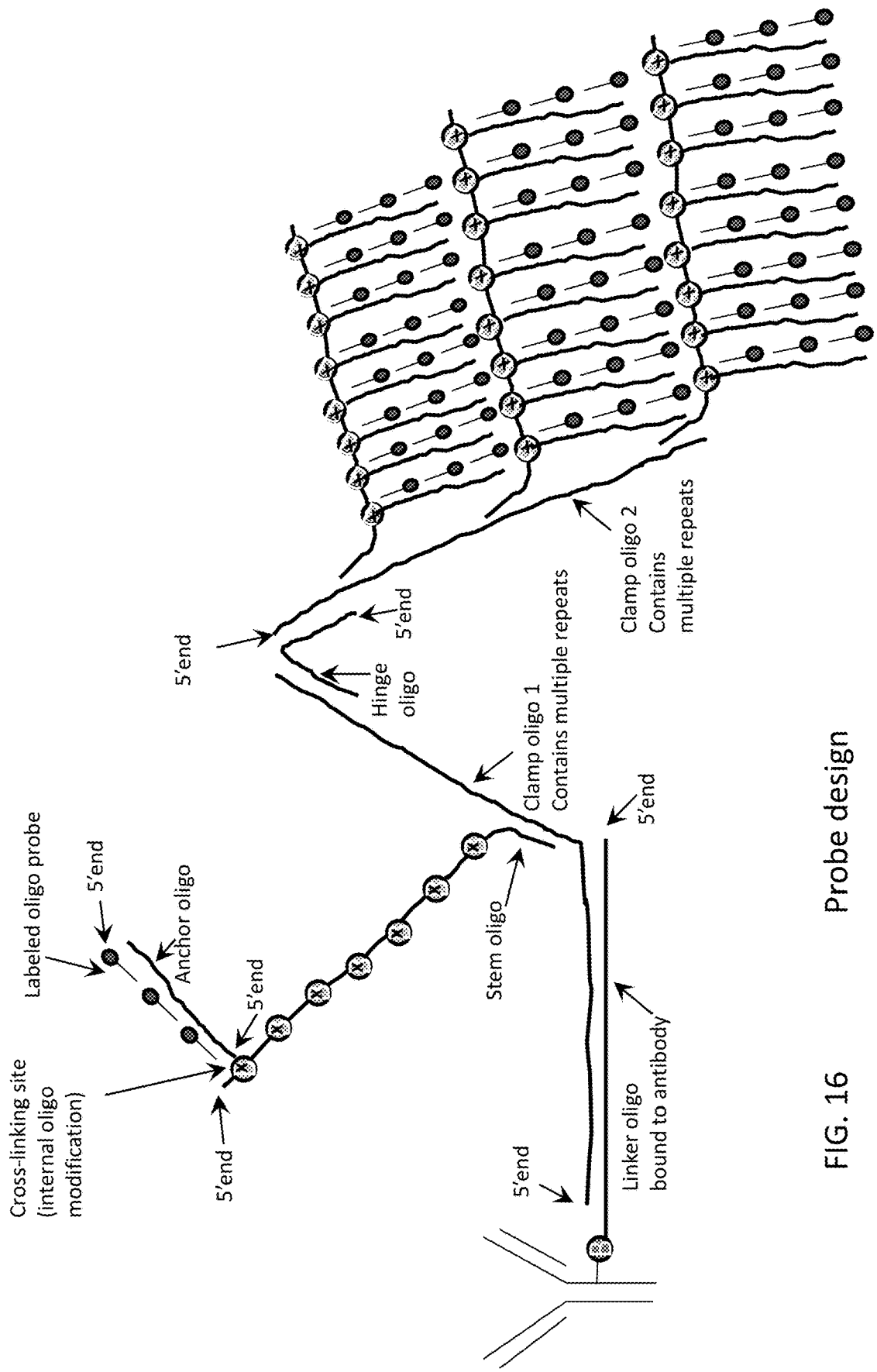
FIG. 16  Probe design

Linker Oligo Sequence:
5'-ACGGGATATCAGTTACGGGGATATCAGTT-(cross-linker)-3' (SEQ ID NO: 9)

Underlined= EcoRV restriction site

Clamp Oligo1 Sequence:
5'-AACTGATATCCCGTAACTGATATCCCGTTTTTTTAGCAACAGTTATCTCGGCACCATTTAGCAACAGTTATCTCGGCACCATTT-AGCAACAGTTATCTCGGCACCATTTTTTGTATGCCAGAATAATCATCGC-3' (SEQ ID NO: 10)

Underlined = SspI Restriction site

Clamp Oligo2 Sequence:
5'- GTATGCCAGAATAATCATCGCTTTTTTAGCAACAGTTATCTCGGCACCATTTAGCAACAGTTATCTCGGCACCA-3' (SEQ ID NO: 11)

Stem Oligo Sequence:
5'-TTGACAGCTGCCGGATTXTTXTTXTTXTTXTTXTTXTTXTTXTTXTT-TTTTT-TGGTGCCGAGATAACTGTTGCT-3' (SEQ ID NO: 12)

X=modified nucleotide or backbone. Options include 5-amino modified thymidine or 5-hydroxy modified thymidine.
Underlined=PvuII restriction site

Anchor Oligo Sequence:
5'-(cross-linker)-TTTTTGACAGCTGCCGGATTTTTTTTGACAGCTGCCGGAT-3' (SEQ ID NO: 13)

Underlined sequence = PvuII restriction enzyme site

Labeled Oligo Probe Sequences:
5'-Label-TCCGGCAGCTGTCAA (SEQ ID NO: 14)
5'-AF488- TCCGGCAGCTGTCAA (SEQ ID NO: 15)
5'-Biotin- TCCGGCAGCTGTCAA SEQ ID NO: 16)
5'-AF594- TCCGGCAGCTGTCAA (SEQ ID NO: 17)

Hinge Oligo sequence:
5'-GCGTTGATTATTCTGGCATAC AAAAAA GCGTTGATTATTCTGGCATAC (SEQ ID NO: 18)

Cross-linker= one option would be amine containing group

FIG. 17      DNA sequences

SeqStain workflow

DBCO-Azide Click Chemistry

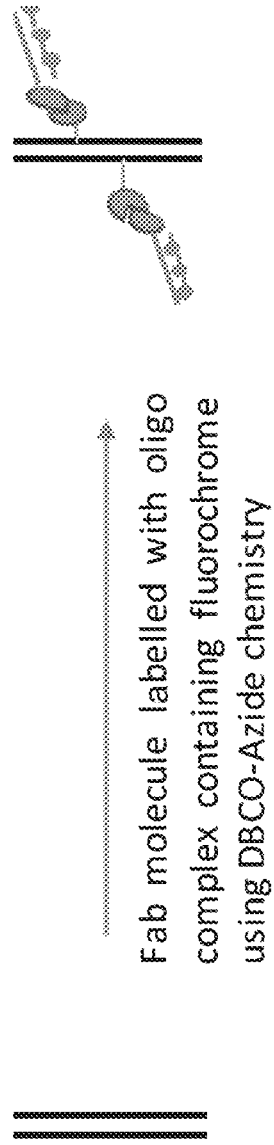
FIG. 23A

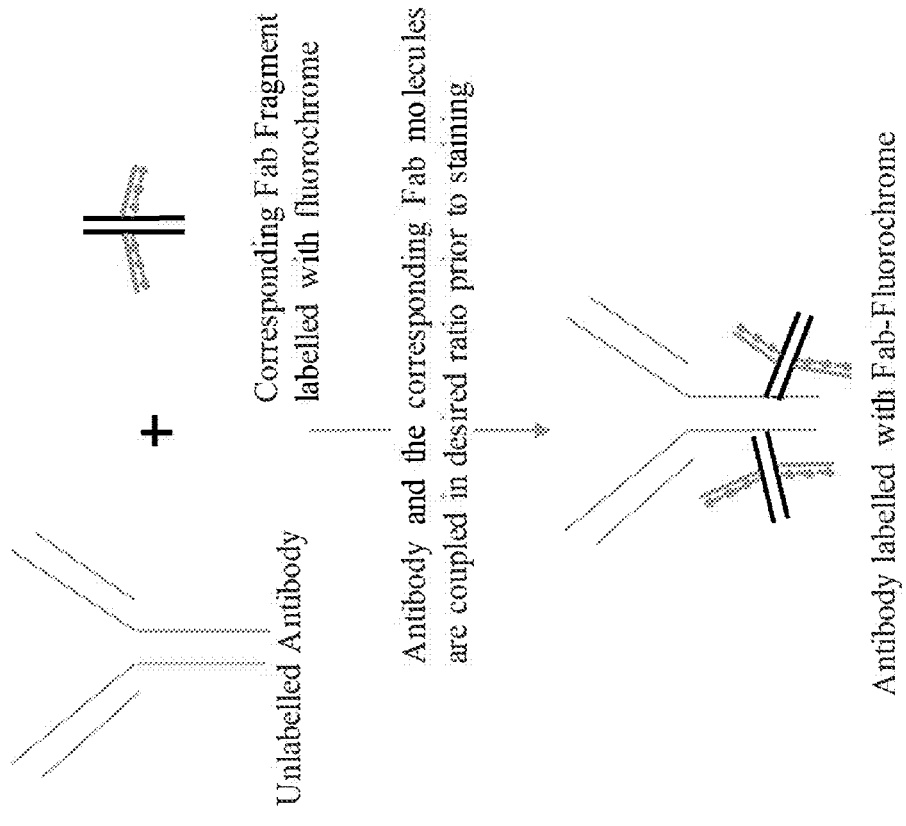

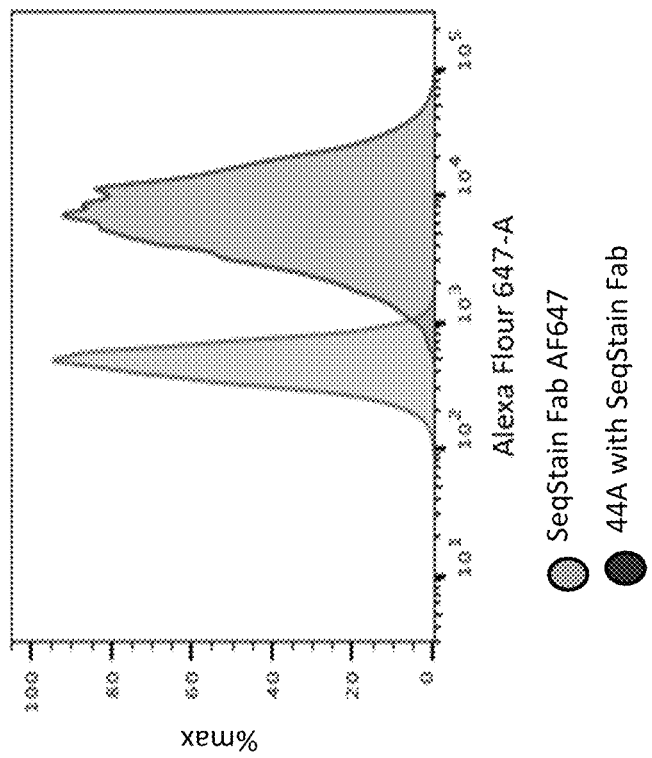
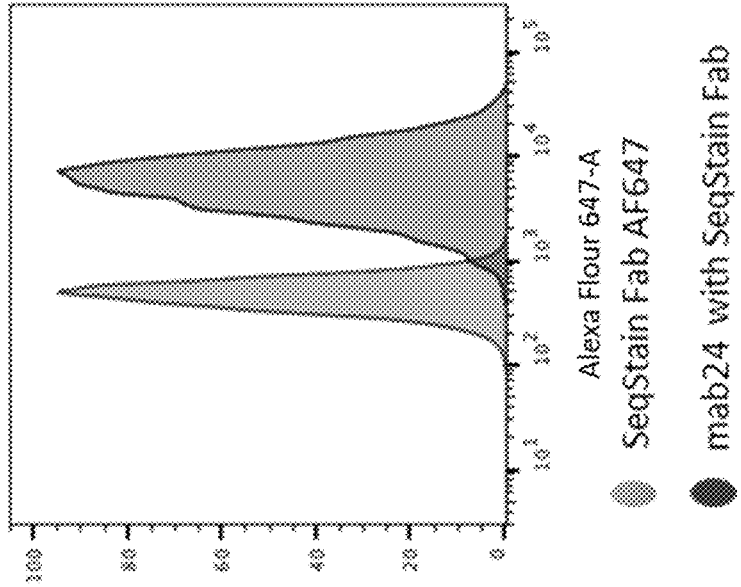
FIG. 24B

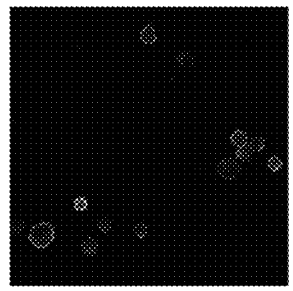
Figure 25C
Staining Round 3
Anti-CD11b(M1/70)-Fab SeqStain Ab
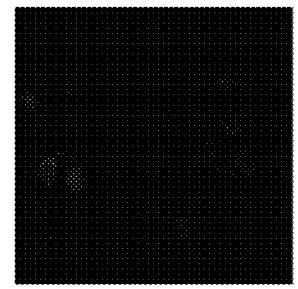
Post Wash
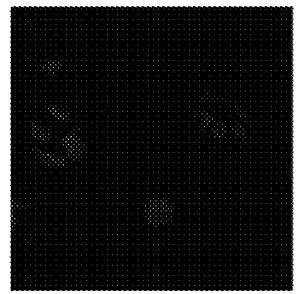
Post destaining
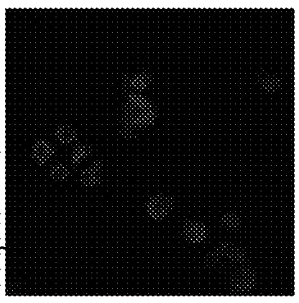
FIG. 25A
Staining Round 1
Anti-CD11b (44A)-SeqStain Fab
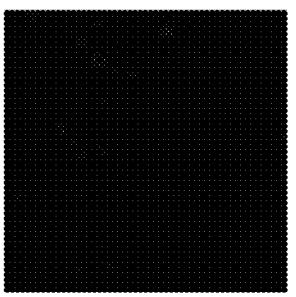
Post Wash
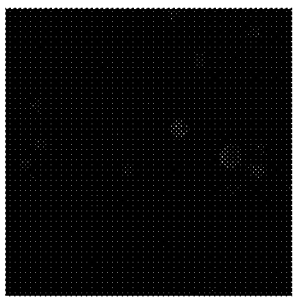
Post destaining
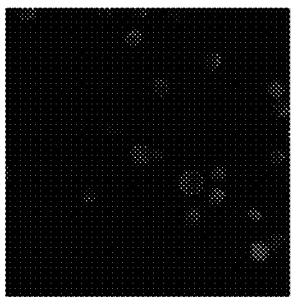
FIG. 25B
Staining Round 2
Anti-CD11b (IB4)-Fab SeqStain Ab

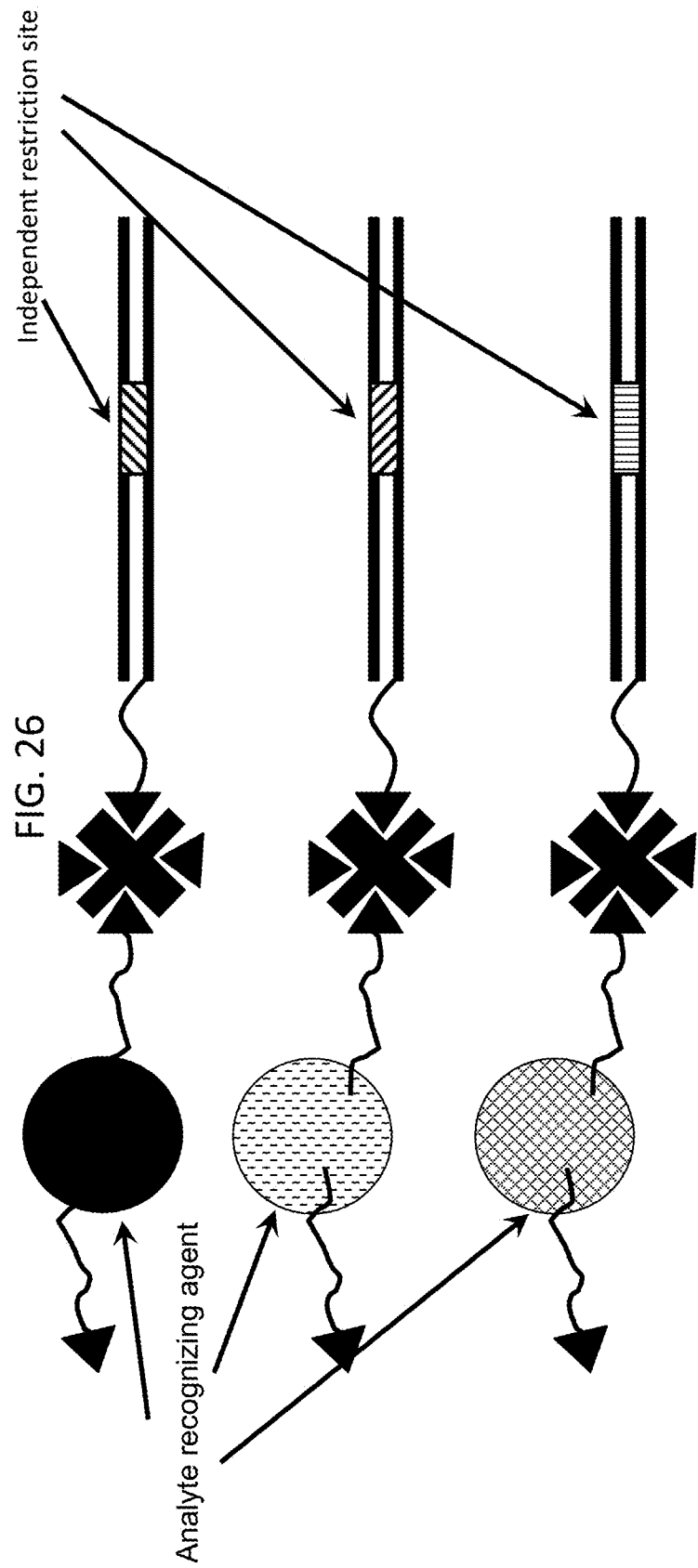

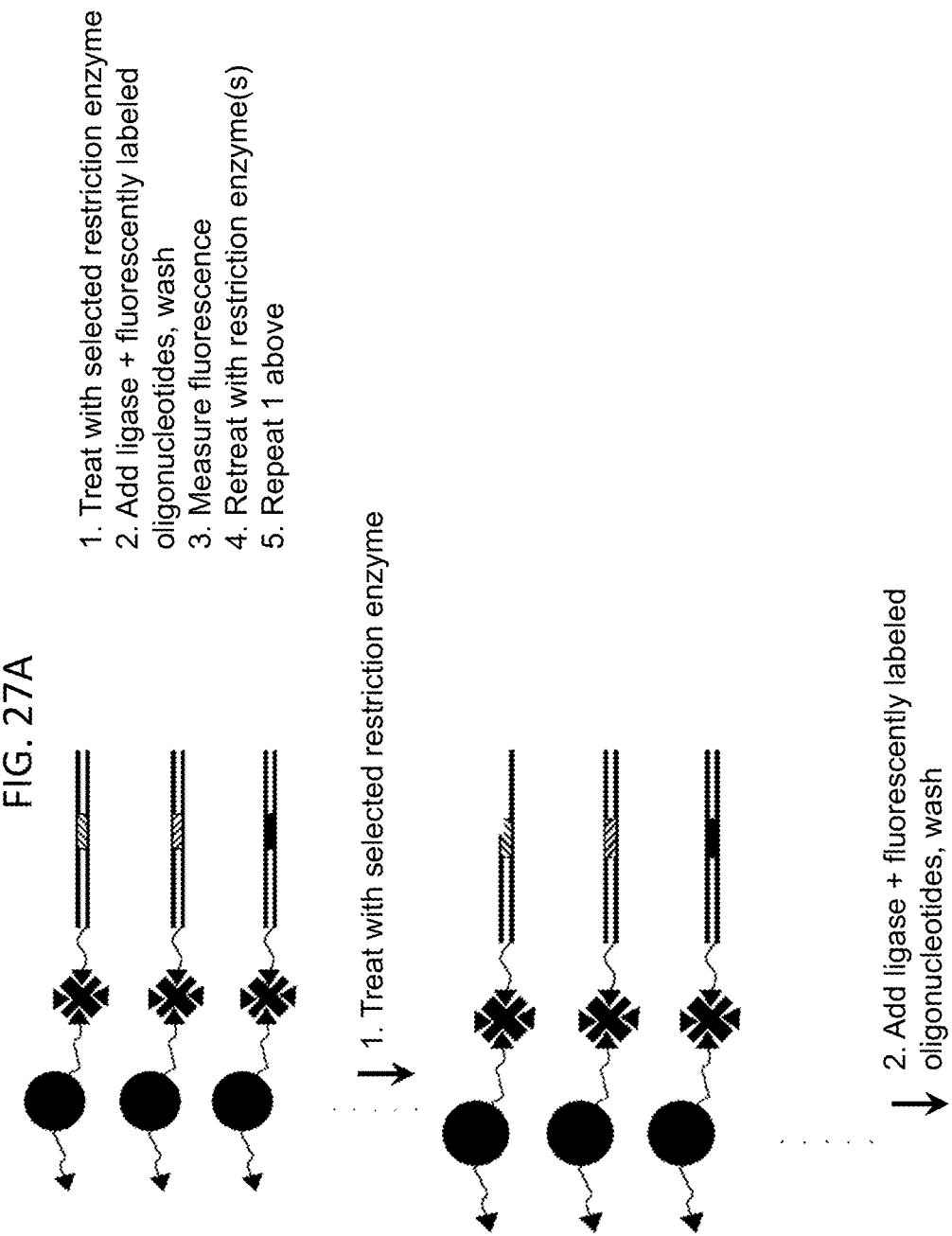

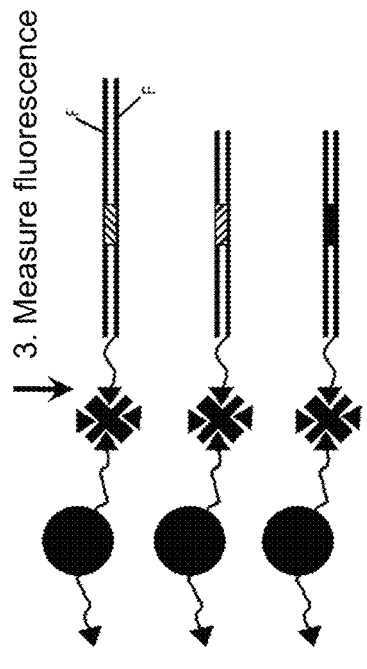
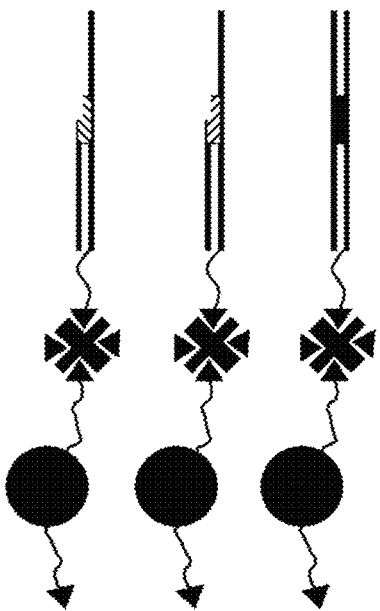
FIG. 27B

1. Treat with selected restriction enzyme
2. Add ligase + fluorescently labeled oligonucleotides, wash
3. Measure fluorescence
4. Retreat with restriction enzyme(s)
5. Repeat 1 above

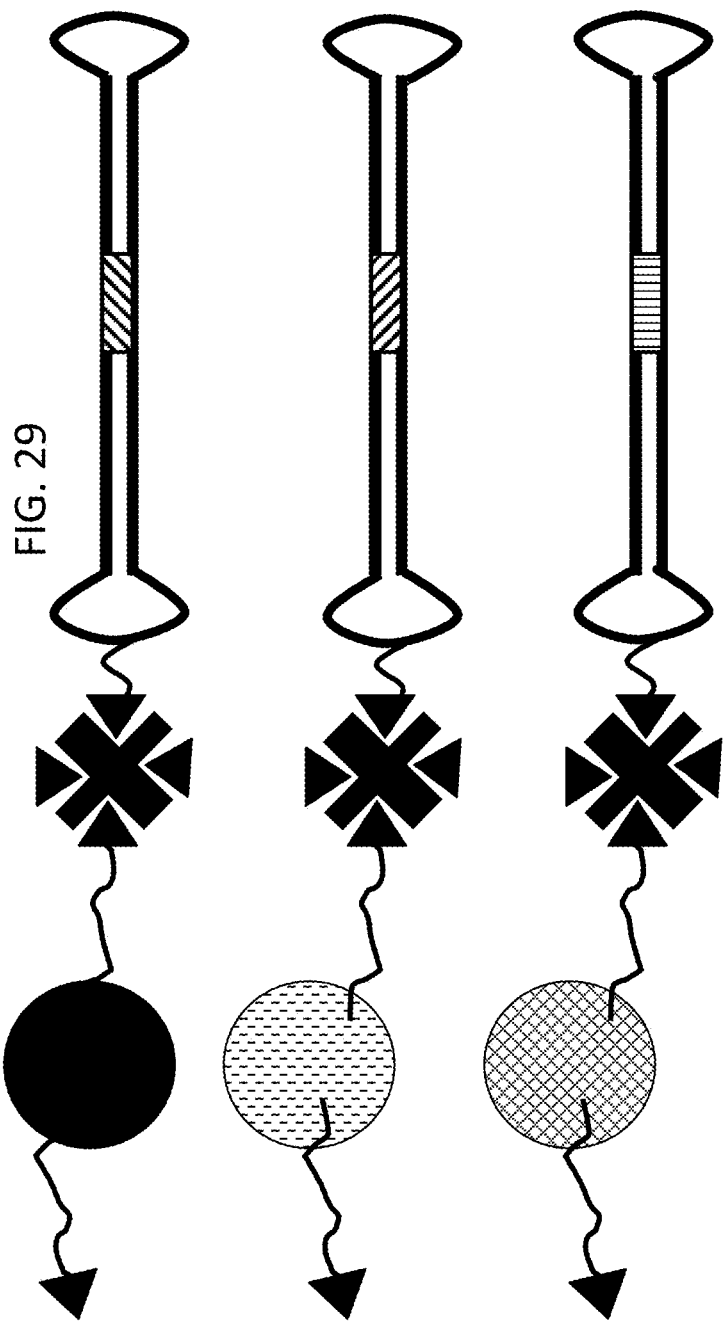

FIG. 30A

Sequences used for preparing SeqStain antibody using Maleimide-Sulfhydryl chemistry

1. Mab linker with EcoRV restriction site

5' {Amine} CCGTAGCAGCAGATATCACAGC-3' (SEQ ID NO: 19)

2. Docking Oligo with EcoRV restriction site

5' TTGACAGCTGCCGGA TTGACAGCTGCCGGA TTGACAGCTGCCGGA TTGACAGCTGCCGGA TTGACAGCTGCCGGA GCTGTGATATCTGCT- 3' (SEQ ID NO: 20)

3. Mab linker with SmaI restriction site

5' {Amine} CCGTAGCACCCGGGACAGC-3' (SEQ ID NO: 21)

4. Docking oligo with SmaI restriction site

5' TTGACAGCTGCCGGA TTGACAGCTGCCGGA TTGACAGCTGCCGGA TTGACAGCTGCCGGA TTGACAGCTGCCGGATTGACAGCTGCCGGA GCTGTCCCGGGTGCT 3' (SEQ ID NO: 22)

5. Fluor Oligos

5' - TCCGGCAGCTGTCAA {AF488} 3' (SEQ ID NO: 23)

5' - TCCGGCAGCTGTCAA {AF594} 3' (SEQ ID NO: 24)

FIG. 30B

Sequences used for preparing SeqStain antibody using DBCO-Azide chemistry

6. Mab linker with EcoRV restriction site

5' ACGGGATATCAGATCAGATACGGGATATCAGATCAGATACGGGATATCAGAT {Azide}3' (SEQ ID NO: 25)

7. Fluorochrome oligos

5' ATCTGATATCCCGT {AF488}-3' (SEQ ID NO: 26)

5' ATCTGATATCCCGT {AF594}-3' (SEQ ID NO: 27)

SEQUENTIAL STAINING FOR MULTIPLEX ANALYSES OF TISSUES AND CELLS

RELATED APPLICATIONS

This application is a National Stage application of International Application No. PCT/US2019/015630, filed Jan. 29, 2019, which claims the benefit of U.S. Provisional Application No. 62/623,866, filed Jan. 30, 2018, both of which are incorporated by reference herein in its their entirety.

SEQUENCE LISTING

The instant application contains a Sequence Listing which has been submitted electronically in ASCII format and is hereby incorporated by reference in its entirety. The ASCII copy, created on Jan. 28, 2021, is named 42960-323631 Sequence listing_2021-01-28_ST25.txt and is 12 KB in size.

TECHNICAL FIELD

The present disclosure relates to compositions relating to detection reagents for sequential staining and analysis of multiple analytes in a sample and methods of using the compositions, in particular to reagents and methods including labile tags for detecting multiple analytes in a sample.

BACKGROUND

There is a need for tagging and analyzing multiple analytes on cells, tissues and biological specimen by imaging. The techniques currently available have shortcomings, including the number of analytes that may be labeled and identified in a single sample.

Currently, light microscopy based techniques are commonly used to probe samples (cells, tissues and other biospecimen) for analytes. Usually, these samples are placed on planar substrates, such a glass slides, and are probed with agents (such as fluorescently labeled antibodies). However, only a few distinct fluorescent labels can be distinguished on a sample, thus limiting the number of independent measurements or analytes that can be determined in each sample. Commonly used techniques are able to provide measurements on only one to four analytes from a single sample, and a few recent reports suggest measuring up to 10 analytes (Remark et al., Science Immunology, 2016; Carstens et al, Nature Comm., 2017.)

What is needed are reagents and methods for analyzing many more analytes on the same sample.

BRIEF SUMMARY

In one aspect, compositions are provided. The compositions include a plurality of analyte detection agents, each analyte detection agent comprising a labile tag operatively coupled to the analyte detection agent, each labile tag comprising a signal that is different from each other labile tag and each analyte detection agent targeting a different analyte. Each labile tag is removable or quenchable without destroying a sample to which the plurality of analyte detection agents is applied and allows for further analysis of the sample with a second plurality of analyte detection agents.

In another aspect, methods for analyzing a sample are provided. The methods include labeling a sample with a plurality of analyte detection agents, each analyte detection agent comprising a labile tag operatively coupled the analyte detection agent, each labile tag comprising a signal that is different from each other labile tag and each analyte detection agent targeting a different analyte. The methods also include detecting the signal generated by each of the plurality of analyte detection agents on the sample, removing the signal from each analyte detection agent; and repeating steps a-c.

BRIEF DESCRIPTION OF THE DRAWINGS

FIG. 1A shows a diagram of an embodiment of a SeqProbe in accordance with the present disclosure.

FIG. 2 shows a diagram of an embodiment of a SeqProbe having a metal-based cross-linker.

FIGS. 4A-4D show diagrams of embodiments of SeqStain probes in accordance with the present disclosure having different tagging agents.

FIGS. 5A-5B show diagrams of embodiments of SeqStain probes having different attachment means for tagging agents.

FIGS. 11A-11H illustrate RAW cells stained with antibody-Streptavidin-oligo1 conjugate.

FIGS. 12A and 12B illustrate oligo-attached antibodies.

FIG. 14 illustrates branched DNA designs for SeqStain probes.

FIG. 15 illustrates the use of an electric field.

FIG. 16 illustrates a hinged probe design.

FIG. 17 illustrates examples of oligonucleotide sequences that may be used for SeqStain probes.

FIG. 22A-22B and 23A-23B illustrate embodiments of SeqStain reagents.

FIG. 24A-24B illustrate flow cytometry staining of cells with SeqStain antibodies.

FIG. 25A-25C show three rounds of staining.

FIG. 26 shows embodiments of SeqStain probes in accordance with the present disclosure.

FIG. 27A-27B illustrate an embodiment of SeqStain workflow.

FIG. 29 shows embodiments of SeqStain probes in accordance with the present disclosure.

FIGS. 30A-30B illustrate sequences for preparing SeqStain antibodies.

DETAILED DESCRIPTION

Figure 1B:
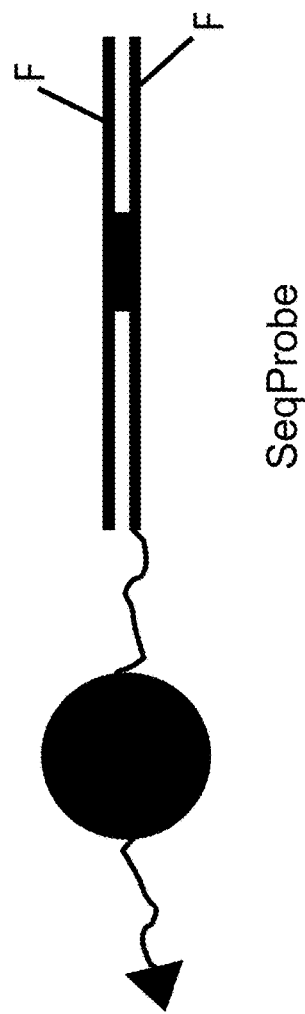
FIG. 1B shows a diagram of an alternative embodiment of a SeqProbe in accordance with the present disclosure.

Unless otherwise defined, scientific and technical terms used in connection with this disclosure shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Generally, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference. As utilized in accordance with this disclosure, the terms defined in this disclosure, unless otherwise indicated, shall be understood to have the meanings as defined herein.

Compositions and methods for detecting many more analytes on the same sample are disclosed. The compositions include sequential probes, also referred to herein as SeqStain probes, that can be used to detect a plurality of analytes in the same sample. The methods use protocols for detecting analytes in samples using the sequential probes and imaging of samples.

Sequential Probe Compositions

The sequential probe (SeqProbe) compositions used to detect an analyte in a sample may include an analyte recognizing agent and a tagging agent/label. The tagging agent is operably connected to the analyte recognizing agent when the sequential probe composition is added to a sample for analyte detection. In some embodiments, the tagging agent is removable from the analyte recognizing agent as described in more detail below. Additional sequential probes having the same type or different type of tagging agent in combination with a different analyte recognizing agent may be added to the sample after the initial tagging agent is removed. In some embodiments, the sequential probe compositions may include one or more functionalized linker. In some embodiments, the sequential probe compositions may include a cross-linker.

Analyte Recognizing Agents

The analyte recognizing agents can comprise any organic or inorganic molecule capable of binding to interact with the analyte to be detected. Non-limiting examples of analyte recognizing agents include proteins, peptides, antibodies, enzyme substrates, transition state analogs, cofactors, nucleotides, polynucleotides, aptamers, lectins, small molecules, ligands, inhibitors, drugs, including small molecules and other biomolecules as well as non-biomolecules capable of binding the analyte to be detected. "Antibody" has its standard meaning and is intended to refer to full-length as well antibody fragments, as are known in the art, including Fab, Fab2, single chain antibodies (scFv for example), nanobodies, monoclonal, polyclonal, chimeric antibodies, or any other portion of an antibody which is capable of specifically binding to an antigen, either produced by the modification of whole antibodies or those synthesized de novo using recombinant DNA technologies. Antibodies used herein are immunoreactive or immunospecific for, and therefore specifically and selectively bind to, for example, proteins either detected (i.e., analytes in biological samples) or used for detection (i.e., binders or probes) in the assays disclosed herein. An antibody as used herein can be specific for any of the analytes, binders, or epitopes disclosed herein or any combinations thereof. In certain embodiments, an analyte itself of the present disclosure can be an antibody or fragments thereof. In this context, "specifically binding" means that the analyte recognizing agent binds to the analyte based on recognition of a binding region or epitope on the analyte. The analyte recognizing agent preferably recognizes and binds to the analyte with a higher binding affinity than it binds to other molecules in the sample. Preferably, the analyte recognizing agent uniquely recognizes and binds to the analyte.

Tagging Agents/Labels

The tagging agent/label of the composition refers to a detectable moiety. In some embodiments, the tagging agents/labels may be operably attached to the analyte recognizing agent prior to addition of the sequential probe to the sample to be tested. In some embodiments, the tagging agents/labels are readily removable from the sample as described below.

Suitable tagging agents/labels encompass a wide variety of possible moieties. By way of non-limiting example, tagging agents//labels include, but are not limited to, a) optical dyes, including colored or fluorescent dyes; b) immune labels, which may be antibodies or antigens; c) enzymes such as alkaline phosphatase and horseradish peroxidase; d) isotopic labels, which may be radioactive or heavy isotopes, e) particles such as colloids, magnetic particles, etc., and combinations thereof such as fluorescent labeled antibodies, and chemiluminescent labeled antibodies.

In some embodiments, the tagging agent includes an oligonucleotide (single or double stranded), such as DNA, RNA, mixture, or a peptide (e.g.; PNA), or another type of polymer. The polymer may contain one or more labels, such as fluorescent labels, that may be on the same or different strands (if more than one). In some embodiments, the tagging agent may also contain a fluorescent quencher. Optionally, the agent might contain enzymatically releasable groups, such as recognition sites for endonucleases, transcription factors (e.g.; ZFPs), etc. The polymer chains may also be either chemically inert or extendable, such as via a DNA polymerase. The polymer chain may also be linear or branched, such as branched DNA (bDNA), dendrimer or DNA origami (using, for example, M13mp18 Single-stranded DNA).

In some embodiments, the tagging agent comprises a fluorescent dye. The fluorescent dye can comprise any entity that provides a fluorescent signal and that can be used in accordance with the methods and devices described herein. Typically, the fluorescent dye comprises a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, non-limiting examples include xanthenes, rhodamines, fluoresceins, cyanines, phthalocyanines, squaraines, bodipy dyes, coumarins, oxazines, and carbopyronines. In some embodiments, for example, where tagging agents contain fluorophores, such as fluorescent dyes, their fluorescence is detected by exciting them with an appropriate light source, and monitoring their fluorescence by a detector sensitive to the characteristic fluorescence emission wavelength. In some embodiments, the tagging agents comprise fluorescent dye labeled antibodies.

By way of non-limiting example, suitable fluorescent reporter dyes may include AlexaFluor dyes, 6-carboxy-fluorescein (FAM), tetrachloro-6-carboxy-fluorescein (TET), 2,7-dimethoxy-4,5-dichloro-6-carboxy-fluorescein (JOE), hexachloro-6-carboxy-fluorescein (HEX), VIC, Cy3, ROX, Texas Red, and Oregon Green. When included as described below, suitable quencher molecules include 6-carboxy-tetramethyl-rhodamine (TAMRA), and Black Hole Quenchers. These dyes are commercially available from Perkin-Elmer, Philadelphia, Pa.; Applied Biosystems, Foster City, Calif.; and Qiagen, Valencia, Calif.

Fluorescent tags can be attached to analyte recognizing agents in many different ways. For example, for antibodies as analyte recognizing agents that are tagged with fluorescently labeled oligonucleotide, the fluorescent oligonucleotide can be attached to the antibody either using a covalent linkage, a non-covalent linkage (such as via streptavidin) or via a metal-coordinate bonds (such as via chloroplatinum-based cross-linkers). In some embodiments, the tagging agent may include DNA prelabeled with fluorophores such as cleavable fluorophores, cleavable DNA and/or ULS-labeled DNA.

In some embodiments, the tagging agent comprises a chemiluminescent label. The chemiluminescent label can comprise any entity that provides a light signal and that can be used in accordance with the methods and devices described herein. Suitable labels include enzymes capable of reacting with a chemiluminescent substrate in such a way that photon emission by chemiluminescence is induced. Such enzymes induce chemiluminescence in other molecules through enzymatic activity. Such enzymes may include peroxidase, beta-galactosidase, phosphatase, or others for which a chemiluminescent substrate is available. In some embodiments, the chemiluminescent label can be selected from any of a variety of classes of luminol label, an isoluminol label, etc. In some embodiments, the tagging agents comprise chemiluminescent labeled antibodies.

In some embodiments, the tagging agent can comprise a bioluminescent compound. Bioluminescence is a type of chemiluminescence found in biological systems in which a catalytic protein increases the efficiency of the chemiluminescent reaction. The presence of a bioluminescent compound is determined by detecting the presence of luminescence. Suitable bioluminescent compounds include, but are not limited to luciferin, luciferase and aequorin.

Detect" and "detection" have their standard meaning, and are intended to encompass detection including the presence or absence, measurement, and/or characterization of an analyte.

Linkers

In some embodiments, the sequential probe composition may include one or more linkers. The linker may be used to connect the tagging agent/label to the analyte recognizing agent. The linker may be directly attached to the tagging agent or be attached via additional moieties as described below. The linker may be functionalized with other groups such as biotin, azide and others to link to other molecules. The linker may also be chemically or enzymatically unstable or cleavable.

Cross-linkers

In some embodiments, the sequential probe composition may include one or more cross-linkers to link multiple molecules, either covalently or non-covalently. Non-limiting examples of cross-linkers include avidin, streptavidin, and disulfide.

In some embodiments, cross-linkers may be used to secure a biological sample to a substrate for detection of the analyte. The substrate may be coated using bifunctional chemical cross-linkers, such as bis-NHS esters, NHS-ester and maleimide cross-linkers, (such as SMCC for labeling antibody/Fab) UV crosslinking agents, UV-crosslinkers attached to maleimide or NHS groups, azido groups, cross-linking using the Staudinger's reaction at one of the ends, etc. to facilitate securing the sample. Additional cross-linking agents may also be used.

Samples

The sample contains the analytes to be detected. The sample can be heterogeneous, containing a variety of components, i.e. different proteins. The sample can be naturally occurring, a biological material. For example, the sample can be a single cell or a plurality of cells, a blood sample, a tissue sample, a skin sample, a urine sample, a water sample, or a soil sample. In some embodiments, the sample comprises the contents of a single cell, or the contents of a plurality of cells. In some embodiments, the sample may be a tissue section or a plurality of tissue sections, for example from a biopsy.

In some embodiments, processing may be performed on the sample prior to detecting the analyte. For example, the sample can be subjected to a lysing step, denaturation step, heating step, purification step, precipitation step, immunoprecipitation step, column chromatography step, centrifugation, etc. In some embodiments, the separation of the sample and immobilization may be performed on native substrates, the analyte of interest, i.e. a protein, or may also undergo denaturation to expose their internal hydrophobic groups. In some embodiments, the sample may be fixed prior to the detection of the analyte. In some embodiments, samples are chemically adhered to the substrate using substrate surfaces pre-coated with agents such as PLL (poly_l_lysine) or 3-Aminopyltriethoxysilane (APES). In some aspects, APES is preferred. To visualize intracellular and nuclear analytes, permeabilization with agents such as Triton-X is carried out. In some embodiments, after placement of samples onto substrates, the substrate-adhered samples are further treated with solutions containing charged molecules, where the charge molecules create a charged environment near the samples and reduce or prevent non-specific binding of tagging agents. Examples of such charged molecules include synthetic oligonucleotides, DNA samples, sheared salmon-sperm DNA, sheared e. *coli* DNA etc. In some embodiments, oligo/DNA containing solution is applied. In another embodiment, such treatment is applied multiple times to the samples.

In some embodiments, the samples are analyzed in the present of an electric or electromagnetic field. Such a field provides increased specificity of binding between sample and tagging agent(s). Such a field also provides improved removal of tagging agent after each round of analysis. Examples include application of electric field from one end to the other end of a perfusion chamber or making one or more surfaces electrically conducting. In an embodiment, ionic molecules are further added to the samples to improve conductance. Examples include histidine, imidazole and other agents. In some embodiments, samples may be placed on indium tin oxide coated glass slides and/or coverslips, for creating an electrically conducting surface. (Sigma Aldrich, No. 703192.) (Su et al., Sosnowski et al. See also, US 20030119028, U.S. Pat. No. 6,083,763.) Additionally, the buffer may contain agents that improve electrical conductance, such as histidine and imidazole.

Non-limiting examples of analytes that can be detected include proteins, oligopeptides and peptides, derivatives and analogs, including proteins containing non-naturally occurring amino acids and amino acid analogs. Other example of analytes that can be detected include carbohydrates, polysaccharides, glycoproteins, viruses, metabolites, cofactors, nucleotides, polynucleotides, transition state analogs, inhibitors, drugs, nutrients, electrolytes, hormones, growth factors and other biomolecules as well as non-biomolecules, as well as fragments and combinations of all the forgoing. pH, ions, divalent ion concentrations etc. can also be measured. (Modi et al., Saha et al., Chakraborty et al.)

Methods of Detection

Detecting the analytes may be by any method known in the art so long as multiple stainings may be accomplished. Analyte detection can be performed by monitoring a signal using conventional methods and instruments, non-limiting examples include, a photodetector, an array of photodetectors, a charged coupled device (CCD) array, etc. For example, a signal can be a continuously monitored, in real time, to allow the user to rapidly determine whether an analyte is present in the sample, and optionally, the amount or activity of the analyte. In some embodiments, superclonal secondaries may be used for detection of a single analyte (a mixture of 2 or more DNA-tagged monoclonal secondary mAbs or secondary Fabs). In some embodiments, infrared-dyes may be used as an additional detection mechanism to increase the number of mAbs that can be read at the same time. In some embodiments, a combination of chemical sensing methodology with multiplex imaging may be used together to obtain a dataset. (See Kwak et al., Baker et al.) In some embodiments, more than one section of serial tissue sections may be used to get data and improve overall data quality for a multiplex result. In certain embodiments, a single tissue section may not be enough to provide high quality data reports so that serial sections may be used to reduce variability.

"Multiplexing" or "multiplex assay" herein may refer to an assay or other analytical method in which the presence and/or amount of multiple targets, e.g., multiple analytes can be assayed simultaneously by using more than one tagging agent/label, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic. In embodiments, using two or more different detection agents, one detection agent, for example a 1° antibody, can bind to or interact with one or more analytes to form a detection agent-analyte complex, and second detection agent, for example a 2° antibody, can be used to bind to or interact with the detection agent-analyte complex.

In some embodiments, multiple detection agents can be used with multiple substrates to provide color-multiplexing. For example, the different chemiluminescent substrates used would be selected such that they emit photons of differing color. Selective detection of different colors, as accomplished by using a diffraction grating, prism, series of colored filters, or other means allow determination of which color photons are being emitted at any position along the fluid path, and therefore determination of which detection agents are present at each emitting location. In some embodiments, different chemiluminescent reagents can be supplied sequentially, allowing different bound detection agents to be detected sequentially.

In some embodiments, a first set of tagging agents may be detected and subsequently removed or blocked and one or more additional sets of tagging agents may be detected. In some embodiments, removal of the set of first tagging agents/labels and additional sets of tagging agents may be accomplished using enzymes, such as exonucleases, endonucleases and restriction enzymes.

Non-limiting examples of agents to remove tagging agents include: Exonucleases and endonucleases, such as DNA polymerase, RNase, T7 exonuclease, Lambda exonuclease, *E Coli* exonuclease, Exonuclease T, exonuclease II, Exonuclease III, exonuclease V, Mung bean exonuclease, micrococcal nuclease, T5 exonuclease, nuclease S1, phosphodiesterase, DNase I, T7 endonuclease, FEN1 endonuclease, nicking endonuclease, restriction enzymes (such as EcoRV, SmaI, Hindlll, BamHI etc), DNase II, benzonase, nuclease P1, ribonuclease, ribonuclease A, ribonuclease H, ribonuclease T1.

Metal ion dependent enzymes, which can be inactivated by using chelators, such as EDTA. Others can be inactivated by heat or pH change.

In some embodiments, methylation-dependent restriction enzymes—that cleave only methylated DNA. Additional agents for removing the tagging agent include Ribozymes, DNAzymes, DNA repair enzymes, RNA hydrolysis reagents, such as metal ions and basic pH buffers. Periodiate to oxidize and break glycol links may also be used in some embodiments. TCEP, beta-mercaptoethanol to reduce and break disulfide bonds may also be used.

After treatment with enzymes, such as a nuclease, the samples can be briefly treated with an overwhelming amount of enzyme substrates, in order to quench any remaining enzyme or perfuse with EDTA to inactivate the enzymes, prior to re-incubation with new sequential probes. For example, if a DNase is used to remove fluorescent tags from the labeled tissues, after washing, the samples can be treated with a solution containing adequate amounts of salmon sperm DNA to quench and block any remaining enzyme. In the case of peptidases and proteases, such as TEV protease, the enzyme can be quenched by heating about 40 degrees Celsius or using iodoacetamide etc. Some enzymes can be blocked using protease inhibitors, such as PMSF, AEBSF etc. Another methodology includes using different types of linkers in between cycles—for example a DNA linker in one cycle and an RNA linker in another cycle. Alternatively or additionally, a double-stranded DNA containing a specific restriction enzyme recognition sequence in one cycle and DNA containing a different restriction enzyme recognition sequence in the next cycle may be used.

The specimen being probed (for example, cells and tissue sections) can be placed on light-transparent surfaces (such as glass cover slips or slides) either directly, or in the presence of additional chemical cross-linkers, that might allow these samples to bind to the surfaces more stably. Methods include using pre-coated surfaces prior to placing the tissue samples. Pre-coating can be with agents, such as poly-1-lysine, bifunctional chemical cross-linkers, such as bis-NHS esters, NHS-ester and maleimide linkers, UV crosslinking agents, UV-crosslinkers attached to maleimide or NHS groups, azido groups, cross-linking using the Staudinger's reaction at one of the ends, etc. In some embodiments, the sample may be placed on glass cover slips or slides and placed in chambers that allow fluid exchange. Examples include tissue samples, such as formalin-fixed tissues sections, placed on glass cover slips in perfusion chambers, such as RC-21BRW and RC-21BR from Warner Instruments.

A non-limiting example of a method of sample staining using sequential probes includes placing tissues and cells on glass cover slips and in perfusion chambers and adding one of more fluorescently labeled antibodies. Usually three different antibodies tagged with different fluorophores can be used as a set of tagging agents followed by imaging the samples. The method includes removing the fluorophores from bound antibodies and re-blocking and re-preparing the samples for probing with additional antibodies, if needed. Optionally, the method includes acquiring a new image to be used as a background for the next set of staining and imaging. The labeling, imaging, blocking, relabeling and reimaging steps may be repeated as many times as needed. In some embodiments, at least 15 different analytes may be detected on the same sample. In some embodiments, at least 20, 25, 30, 35, 40, 45, 50, 55, 60, 65, 70, 75 or over 100 different analytes may be detected on the same sample, including all integers in between.

EXAMPLES

Figure 28:
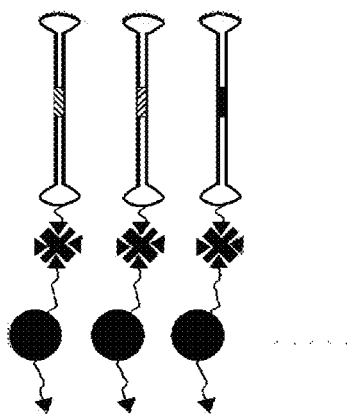
FIG. 28 illustrates an embodiment of SeqStain workflow.

A schematic depiction of a SeqProbe (sequential probe), is shown in FIGS. 1A and 1B. The sequential probe includes a combination of an analyte recognizing agent and one or more removable tags, for example fluorescent tags. A linker is used to attach the fluorescent tag to the analyte recognizing agent. The linker can either be directly attached to the fluorescent tag or be attached via additional moieties. The linker can be functionalized with other groups, such as a biotin. In the case of a free biotin in the linker, biotin-binding agents, such as streptavidin, can be used to attach a fluorescent tag to the agent. Furthermore, the linker may be cleavable, for example, it may contain disulfide linkage, or glycol, that can be cleaved using periodate, or photocleavable groups, or peptide sequences that can be selectively cleaved using peptidases, such as TEV protease. Fluorescently labeled oligonucleotides, such as fluorescently labeled single or double-stranded DNA, can be attached to the analyte recognizing agents via a linker. In the case of a streptavidin attached agent, the oligonucleotides can be functionalized with biotin at one end, for linking it to the analyte recognizing agent. One or more fluorescent groups can thus be attached to a single analyte recognizing agent at a time. The attached fluorescent tags can be removed in such sequential probes via treatment with cleavage agents, such as exonuclease and endonuclease enzymes. In this example, double-stranded DNA, with one or both strand with one or more flurochrome is shown. FIG. 1A also depicts region that contains a restriction enzyme recognition sequence (R). Treatment with either a nuclease or a restriction enzyme would release the fluorescent tag, that can be washed away from a sequential probe immobilized on specimen being probed. The attached oligonucleotides can also be used in rolling circle amplification or tandem repeat amplification etc. Additionally, the fluorescent tags on oligonucleotides can be attached via a cleavable chemical linker, such as a disulfide or a glycol. FIG. 26 depicts several different SeqStain probes, each having a distinct analyte recognizing agent and independent restriction site. FIG. 28 depicts SeqStain probes having distinct analyte recognizing agents and distinct tagging agents/labels.

A schematic depiction of a SeqProbe is show in FIG. 2. As shown, the analyte recognizing agent is linked to the fluorescent tag via a non-covalent, metal coordination chemistry, such as using platinum reagents (such as dichloro Pt (II) reagents, such as cis-platin). In this example, double-stranded DNA, with each strand labeled with a fluorophore is shown. FIG. 2 also depicts a region that contains a restriction enzyme recognition sequence. Treatment with either a nuclease or a restriction enzyme would release the fluorescent tag, that can be washed away from a SeqProbe immobilized on specimen being probed.

Figure 3A:
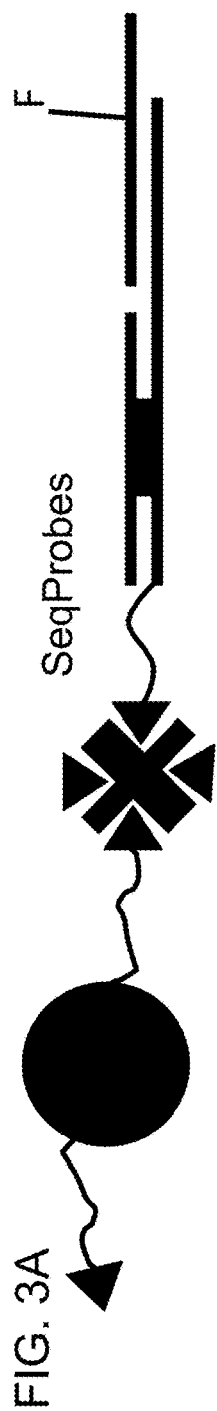
FIGS. 3A-3D show diagrams of embodiments of SeqStain probes in accordance with the present disclosure having different tagging agents.
Figure 3B:
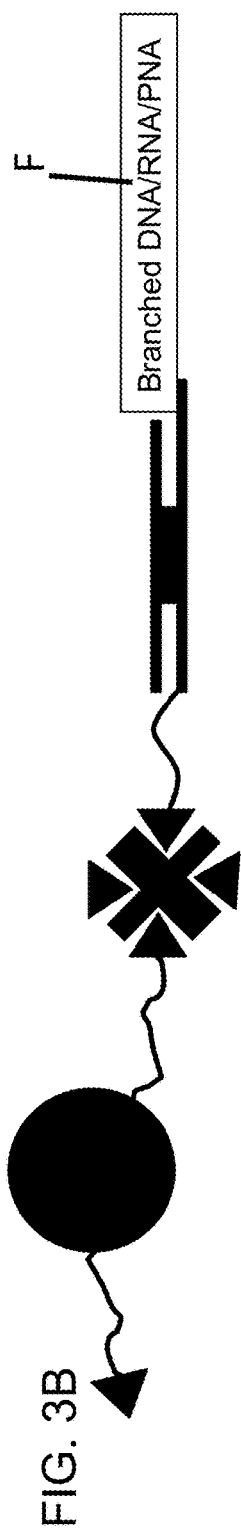
Figure 3C:
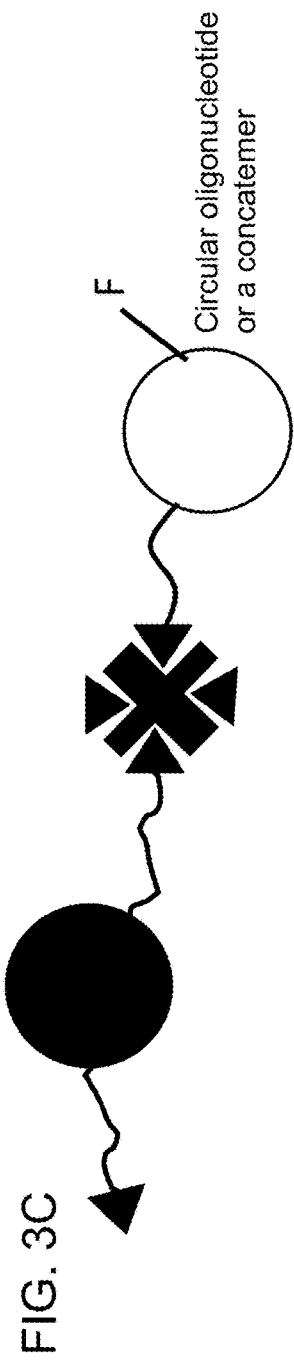
Figure 3D:
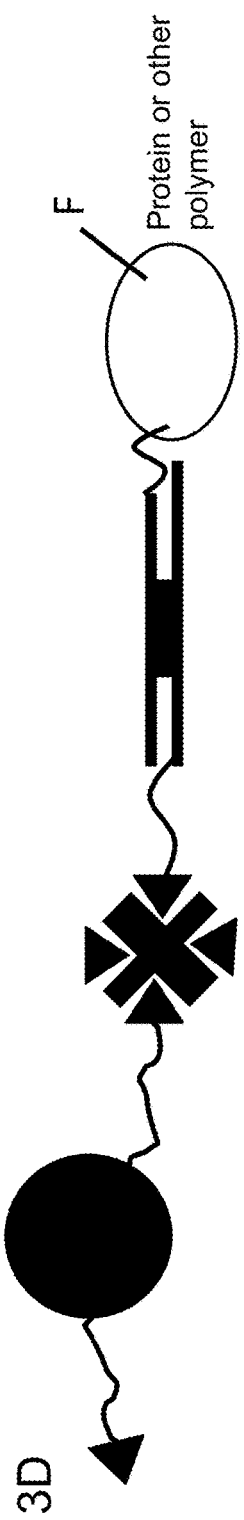

Schematic depictions of additional SeqProbe designs, with varying forms of fluorescent tags are shown in FIGS. 3A-3D. FIG. 3A. Shows fluorescently-labeled oligonucleotide that non-covalently attaches to a single-stranded of double-stranded oligonucleotide (for example, via base-pairing). FIG. 3B. The fluorescently-labeled oligonucleotides assemble into a branched-DNA (b-DNA) system, such that many fluorophores can be attached to each linker. Each oligonucleotide can have one or more fluorphores on it. FIG. 3C. A fluorescently-labeled circular or concatemer oligonucleotide is used. FIG. 3D. An oligonucleotide is used to attached a fluorescently-labeled peptide, protein or other polymer(s) to the rest of the molecule.

Schematic depictions of additional SeqProbe designs, with varying forms of fluorescent tags are shown in FIGS. 4A-4D. FIG. 4A shows fluorescently labeled single stranded oligonucleotide as a fluorescent tag. The single-stranded oligonucleotide may adopt additional secondary and tertiary folded structure, such as a hairpin loop etc. This could also be circularized and used in rolling circle amplification or tandem repeat amplification etc. FIG. 4B. A fluorescently labeled peptide, small molecule, protein or minor or major DNA groove binders are used to impart fluorescent tags to unlabeled or quencher labeled oligonucleotides linked to the rest of the molecule. FIG. 4C. One or more fluorescently labeled oligonucleotides are attached to an antigen recognizing agent via an additional oligonucleotide (single stranded or double stranded) as a linker. FIG. 4D. An oligonucleotide is used to bind to one or more fluorescently labeled proteins, such a streptavidin, via an intervening biotin linkage.

Schematic depictions of additional SeqProbe designs, with varying ways of attaching fluorescent tags are shown in FIGS. 5A and 5B. FIG. 5A. The fluorescent tag is linked via a disulfide linker that can be cleaved using a reducing agent, such as TCEP. FIG. 5B. The tag is linked via other cleavable linkers, such as glycol, that can be cleaved using periodate, or via photocleavable groups, or via peptides that can be selectively cleaved using peptidases, such as TEV protease. Additionally, the linker can be modified with a fluorophore or horse radish peroxidase.

Figure 6:
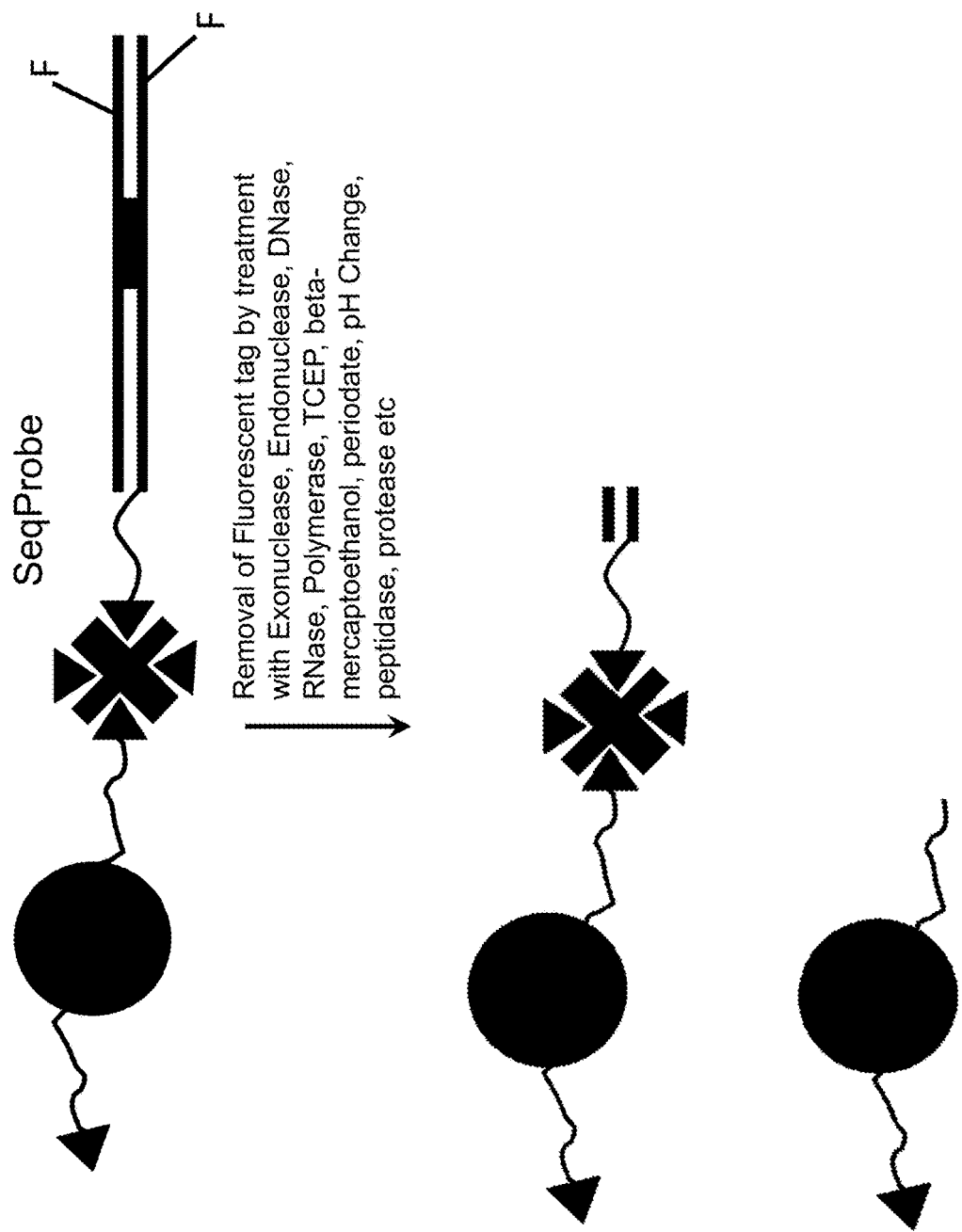
FIG. 6 illustrates an embodiment of a method for removing a tagging agent from an analyte recognizing agent in accordance with the present disclosure.
Figure 7A:
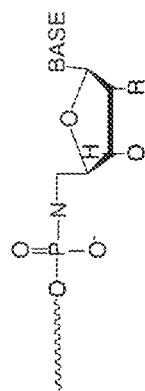
FIGS. 7A-7D illustrate methods for removing a tagging agent in accordance with the present disclosure.
Figure 7B:
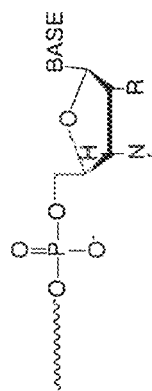
Figure 7C:
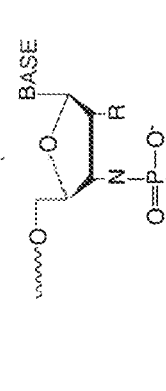
Figure 7D:
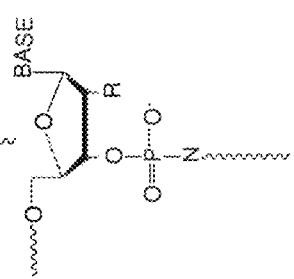

A schematic depiction of methods for removing fluorescent labels from SeqStain probes is shown in FIG. 6.

FIGS. 7A-7D show various modified phospho-linkages in oligonucleotides that make the oligonucleotides sensitive to cleavage. Shown are phosphoramidate linkages that are sensitive to pH changes, such that pH less than 6.0 makes these binds labile. This linkage can be used to cleave fluorescently tagged oligonucleotides.

Figure 8:
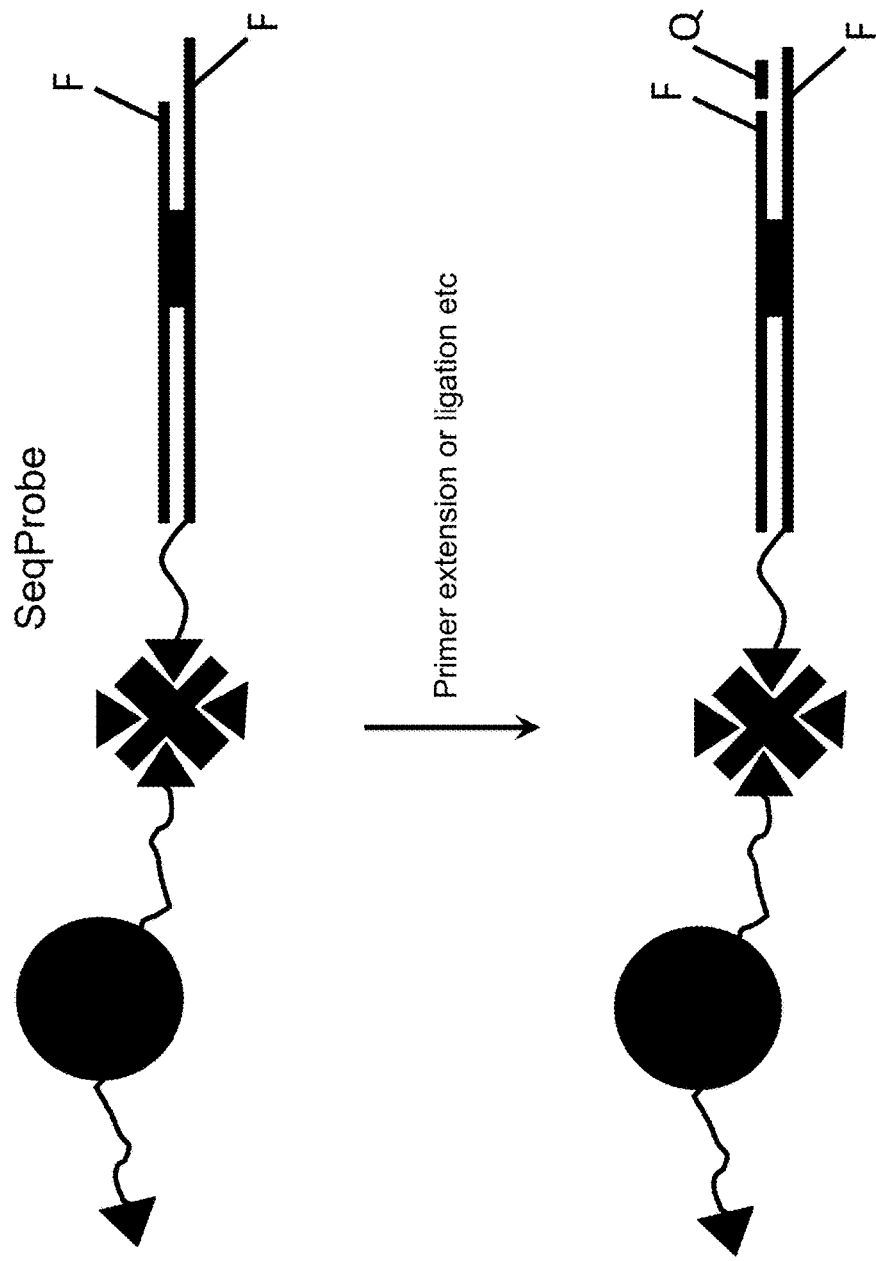
FIG. 8 illustrates an embodiment of a method for reducing a signal of a SeqProbe.

A schematic description of another methodology to reduce the fluorescent signal in SeqStain probes is shown in FIG. 8. Here, addition of a quencher molecule, either via primer extension or via oligonucleotide ligation can result in quenching of fluorescence from SeqStain probes such that new fluorescence signal can be obtained in the new cycle of sample staining.

Figure 9:
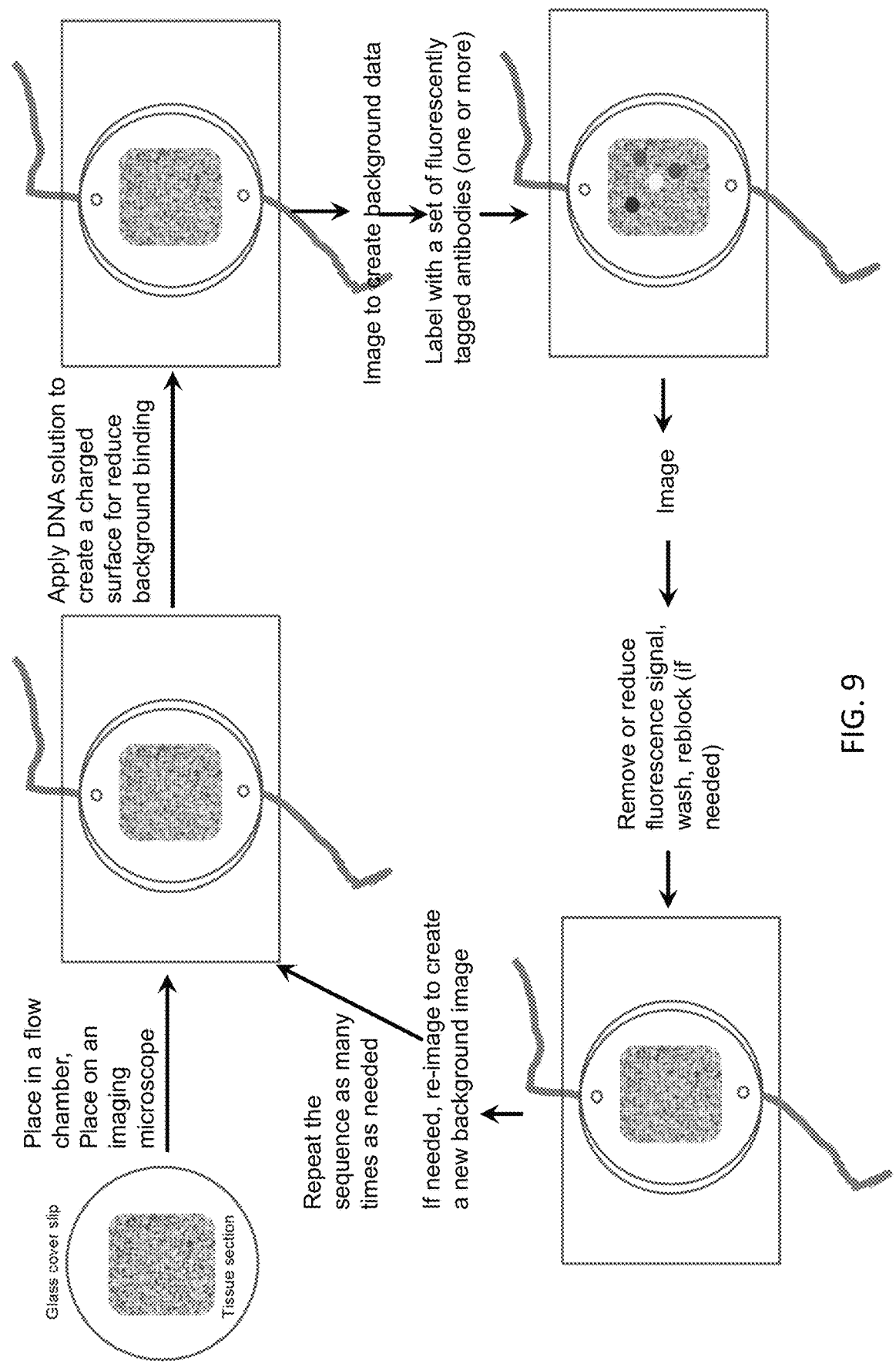
FIG. 9 illustrates an embodiment of a method for sequential staining of a sample with SeqStain probes in accordance with the present disclosure.

A schematic description of the SeqStain methodology that uses cleavable fluorophores linked to analyte detecting agents is shown in FIG. 9. As an example, tissue sections on glass cover slips are placed in flow chambers on top of an imaging microscope. Next, a set of antibodies linked to fluorescent tag via double-stranded DNA, each tagged with a unique fluorophore, are introduced into the chambers and incubated for a set period. Subsequently, the chambers are washed and imaged, to register the position of each antibody. Next, the fluorophores on the antibodies are removed by treatment with DNase. The chambers are subsequently washed and, if need be, reimaged to acquire a new starting image of the tissue. Subsequently, a new cycle of antibody incubation can be started. This sequential staining, imaging and fluorescence label removal steps can be performed as many times as needed to perform multiplex analyses of the biospecimen.

Figure 10:
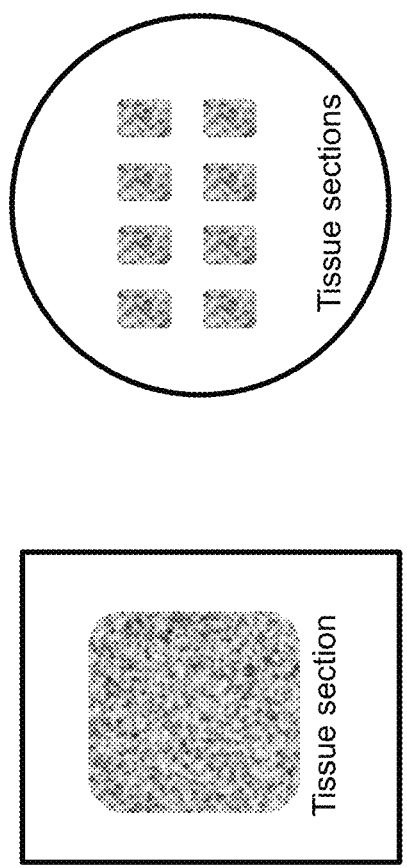
FIG. 10 illustrates embodiments of samples that may be probed with the SeqStain probes in accordance with the present disclosure.

A schematic description of placement of samples on imaging planar surfaces is shown in FIG. 10. The surfaces can be of any shape and any size, for example, circular or square or rectangular. Additionally, one or more samples can be placed in on a single surface such that one or more samples can be processed in the SeqStain protocols.

Example: Sequential Staining of Cultured RAW Cells 25 mm round glass coverslips were coated with poly-L-lysine and the coverslips were placed in tissue culture dishes to culture murine RAW 264.7 macrophage cells on the coverslips over night in a 37°C incubator. Subsequently, the cell monolayer was washed with PBS and the cells were fixed using a solution of 4% paraformaldehyde for 20 minutes at room temperature. The cells were washed twice with PBS and permeabilized with 0.5% Triton-X for 15 minutes at room temperature. Subsequently, the cells were washed twice with PBS and the cover glass was mounted into a perfusion chamber for imaging assays. The chamber was created by placing a rubber gasket in between two glass coverslips. The chamber was attached to an inlet and an outlet tube for perfusion. Subsequently, the cells were blocked by perfusing the chamber with blocking buffer containing 4% BSA and 100 ug/ml sheared salmon sperm DNA in PBS and incubated for 1 hr at room temperature. Separately, the labeling mixture was prepared by mixing, at room temperature, a biotinylated anti-CD11b antibody (20 nM) with purified streptavidin and biotinylated double-stranded DNA (dsDNA) oligonucleotide (oligo1) at a 1:1:3 molar ratio. Oligo1 contains a terminal fluorophore Alexa-Flour488 (AF488) and an engineered EcoRV restriction site. Following blocking, the chamber was stained by perfusion with anti-CD11b antibody-oligo AF488 complex (CD11b-oligoAF488) and incubated at room temperature for 30 minutes. The cells were washed with PBS-T continuously for 5 minutes and subsequently imaged for CD11b staining (FIG. 11A). The results show high fluorescent staining of CD11b on these cells. Subsequently, we removed the antibody-linked fluorophore by treating the samples with a restriction endonuclease. The chamber was perfused with PBS containing EcoRV restriction enzyme to cleave the oligo at the EcoRV restriction site. We monitored the disappearance of localized fluorescence signal by imaging. Here, the cells were imaged every 5 minutes following restriction digestion. Surprisingly, perfusion of the enzyme alone at this concentration itself resulted in gradual removal of signal as visualized by imaging every 5 minutes (FIG. 11B-11F). More surprisingly, perfusion and washing resulted in complete removal of the fluorescent signal (FIG. 11G). Subsequently, the restriction enzyme was inactivated by perfusing the chamber with a solution containing 0.5M EDTA. To determine if the cells can be restained, we re-perfused the cells with anti-CD11b antibody-oligo AF488 complex (CD11b-oligoAF488) and incubated at room temperature for 30 minutes. Even more surprisingly, the imaging results show that the reagent was able to restain the cells (FIG. 11H), suggesting that the perfusion protocol and assay does not result in loss of cells. This process can be repeated multiple times with antibodies against other analytes.

Example design of antibody-oligo conjugates: FIG. 12 shows a depiction of biotinylated anti-CD11b and anti-CD45 antibodies conjugated to biotynylated oligo1 AF488 and oligo2 AF594 respectively using purified streptavidin. Oligo1 contains an EcoRV restriction site, while Oligo2 contains a SmaI restriction site.

Figure 13:
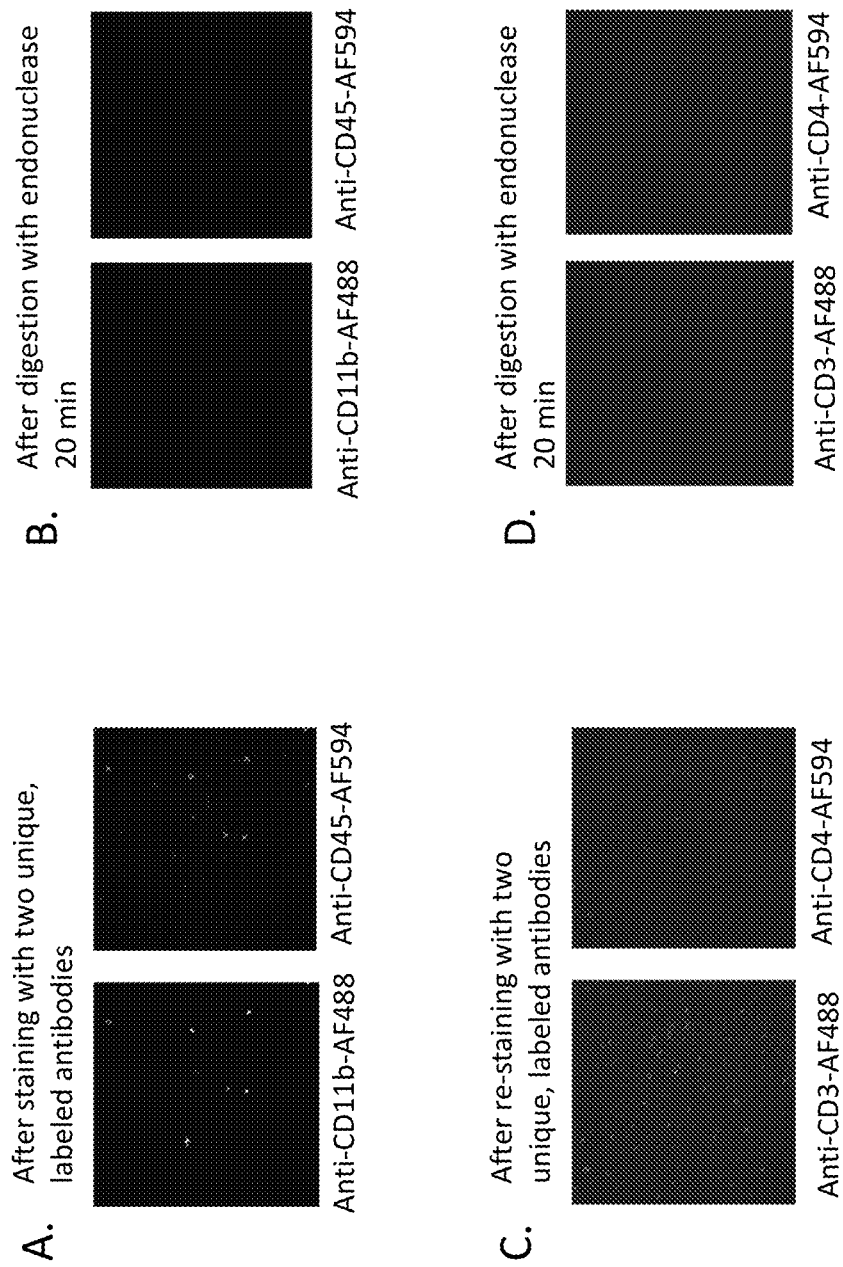
FIGS. 13A-13D illustrate staining, destaining and restaining of the same sample with two rounds of SeqStain antibodies with two antibodies in each round.
Figure 18:
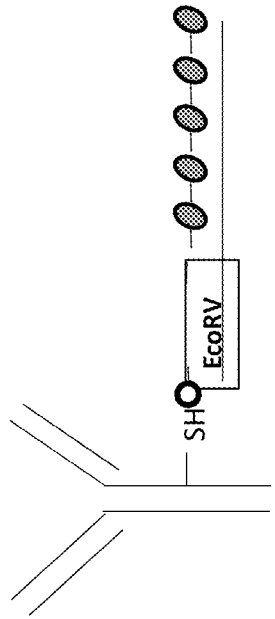
FIG. 18 illustrates an example of maleimide labelling of an antibody.
Figure 19:
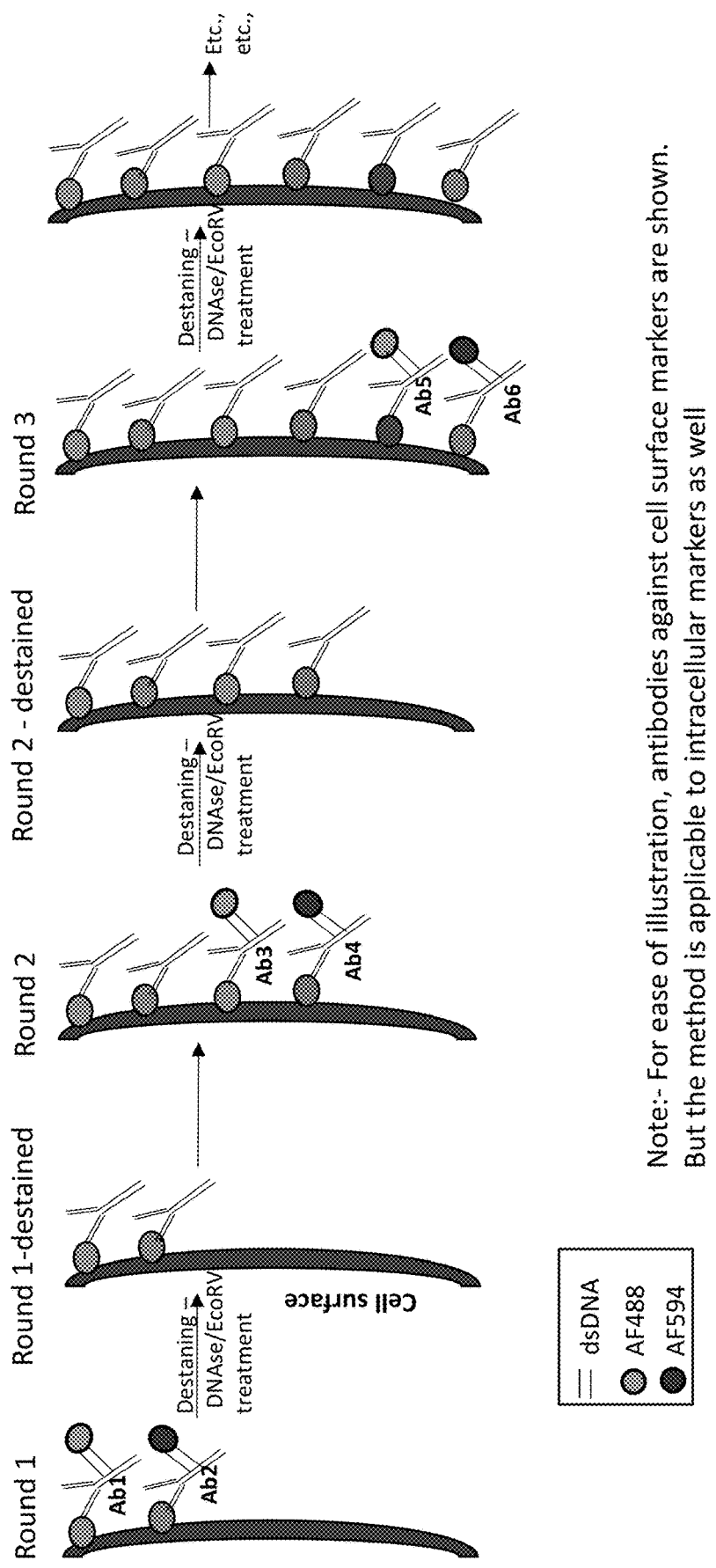
FIG. 19 illustrates an embodiment showing three rounds of SeqStain.
Figure 20:
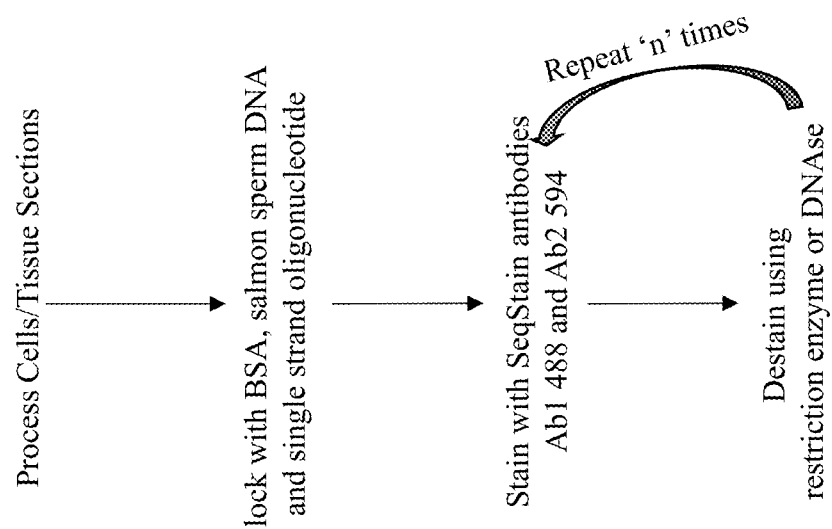
FIG. 20 illustrates an embodiment of SeqStain workflow.

Example: Sequential multiplex staining of mouse splenocytes: Single cell suspension of splenocytes was prepared from the freshly isolated spleen of wild type C57BL/6 mouse. The red blood cells were lysed using BD pharmlyse buffer system and the splenocytes were washed twice with complete media. After the last wash, the cells were counted and fixed using 4% paraformaldehyde. The fixed cells were plated at $2 \times 10^6$ cells per well on APES-coated glass cover slips in a 6-well tissue culture plate and incubated at room temperature for 30 minutes. The cells were then washed twice with PBS and permeabilized using 0.5% Triton-X for 15 minutes. The cells were washed twice with PBS and mounted onto the perfusion chamber. The chamber was perfused with blocking buffer containing 4% BSA and 100 ug/ml sheared salmon sperm DNA and incubated for 1 hr. Separately, biotinylated anti-CD11b antibody was conjugated at 20 nM concentration with purified streptavidin and biotinylated dsDNA oligo1 at 1:1:3 molar ratio. In another separate reaction, biotinylated anti-CD45 antibody was conjugated at 20 nM concentration with purified streptavidin and biotinylated dsDNA oligo2 at 1:1:3 molar ratio. Oligo1 contains an engineered EcoRV restriction site and a terminal Alexflour488 while, oligo2 contains an engineered SmaI restriction site and a terminal Alexaflour594. Following blocking reaction, the chamber containing splenocytes on glass coverslips was perfused with a solution containing both anti-CD11b and anti-CD45 antibodies conjugated with oligos. The splenocytes were imaged for CD11b and CD45 staining (FIG. 13A) and showed good staining. Following imaging, the cells were perfused with a double digestion mix containing both EcoRV and SmaI enzymes and the cells were imaged every 5 minutes. Surprisingly, after 20 min of digestion with restriction enzymes, the localized fluorescent signal was significantly reduced and washing completely removed this signal (FIG. 13B). Next, the restriction enzymes were inactivated by perfusing 0.5M EDTA, followed by 10 minute incubation. Next, we stained these cells with a new set of antibodies. For this round of staining, biotinylated anti-CD3 and biotinylated anti-CD4 antibodies were prepared as above using purified streptavidin and biotinylated oligo1 AF488 and biotinylated oligo2 AF594 respectively. The chamber containing splenocytes on glass cover slips was perfused with a solution containing both antibodies and the cells were imaged for CD3 and CD4 staining. The results show high staining for both (FIG. 13C). Following imaging, the cells were perfused with a double digestion mix containing both EcoRV and Smal enzymes. The cells were imaged every 5 minutes. Again, surprisingly, both signals were diminished follow endonuclease digestion and washing (FIG. 13D). The results here clearly show that this novel technique allows sequential staining and removal of fluorescent signal from fixed samples, without any loss or harm to the sample from these reagents. It was surprising to find that the endonuclease treatment did not damage the fixed samples.

Example design and sequences of branched DNA (bDNA) (FIG. 14).

Example: Use of electric field. Samples can be applied to conducting surfaces in many ways. The entire surface can be made out of conducting material (FIG. 15A) or only part of it could be conducting (FIG. 15B). Alternatively, the sample can be on a non-conducting surface and other parts of the chamber can have conducting material present (FIG. 15C). An example sketch shows how samples can be interrogated in the presence of an electric current (FIG. 15D). In one embodiment, the chambers may also contain a temperature control module, such as a heater or a cooler.

Example: Schematic depiction of a hinged probe design that can be used to link multiple fluorescently labeled tags or probes to an analyte recognizing agent, such as an antibody (FIG. 16). In one embodiment, such cleavable probes are prepared using multiple, linked oligonucleotides, containing optional restriction site sequence. Multiple oligonucleotides may be linked together using one or more hinge probes. Example oligonucleotide sequences are shown in FIG. 17.

Example: Antibody preparation for SeqStain methods. Antibodies were conjugated using maleimide-sulfhydryl chemistry to mab linker DNA oligo. By way of non-limiting example antibodies tested were anti-CD45, anti-CD11b, anti-Golgin 97, anti-Ki67. For maleimide labelling of antibodies used in these examples, a maleimide-modified oligonucleotide or oligonucleotide mixture is co-incubated with antibody (or Fab) in the presence of TCEP as a disulfide reducing agent. This results in an efficient crosslinking of antibody with (labeled or unlabeled) oligonucleotide(s). Unreacted reagents are removed by column filtration. Alternatively, creation of antibody-dna conjugate may be by a sequential reaction—where antibody is first reduced with TCEP, purified using fitlration columns and then reacted with maleimide modified oligonucleotide(s).

Conjugation was verified by running the samples on a denaturing 4-12% SDS gel. Shift in the gel of the conjugated antibody corresponding to the molecular weight of the mab linker relative to the non-conjugated antibody showed conjugation. Following conjugation, the antibody was annealed to complex containing the docking oligo and fluorochrome oligo. The docking oligo and the flourochrome oligo was pre-annealed at 1:5 molar ratio. Successful annealing was verified by a gel shift assay, where samples were run on a 4% agarose gel, run at 40V for 3 hours.

SeqStain Examples: RAW cells were stained with anti-CD45 antibody. Anti-CD45 Ab was conjugated using male- imide-sulfhydryl chemistry to DNA oligo containing a restriction site and fluorochrome AF488. Raw cells were stained with this antibody (anti-CD45 SeqStain Ab) and destained using either restriction enzyme EcoRV or DNAseI. As a control, the DNA oligo complex without the antibody was used to stain the RAW cells. Successful staining of the RAW cells with anti-CD45 SeqStain antibody was detected by fluorescence imaging and removal of the signal was also achieved with both EcoRV and DNAseI digestion. Post destaining and post wash images both showed removal of the signal.

Figure 21A:
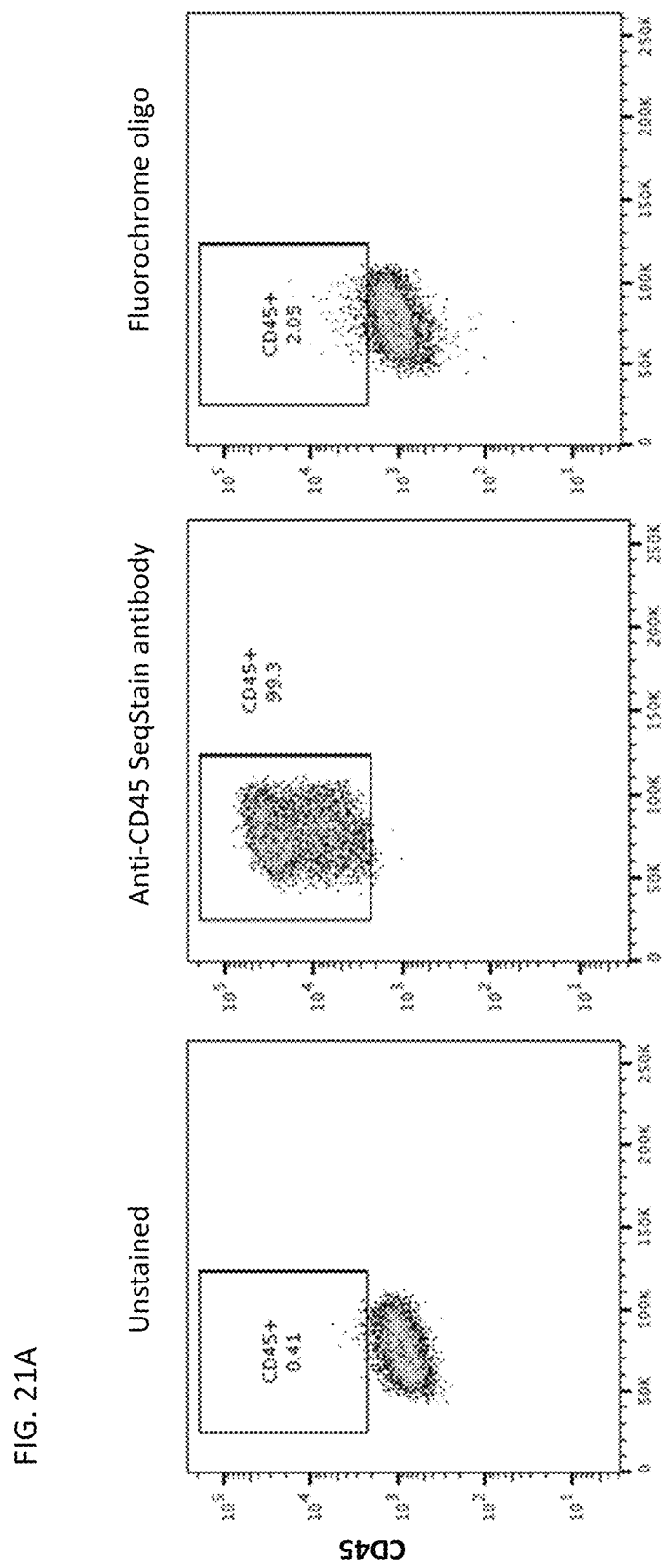
FIG. 21A-21D illustrate flow cytometry staining of cells with SeqStain antibodies.
Figure 21D:
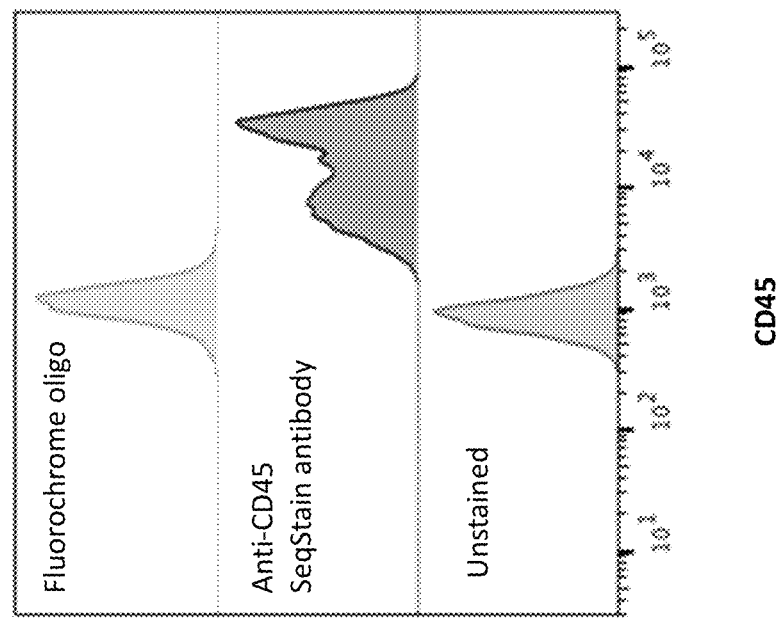
Figure 21B:
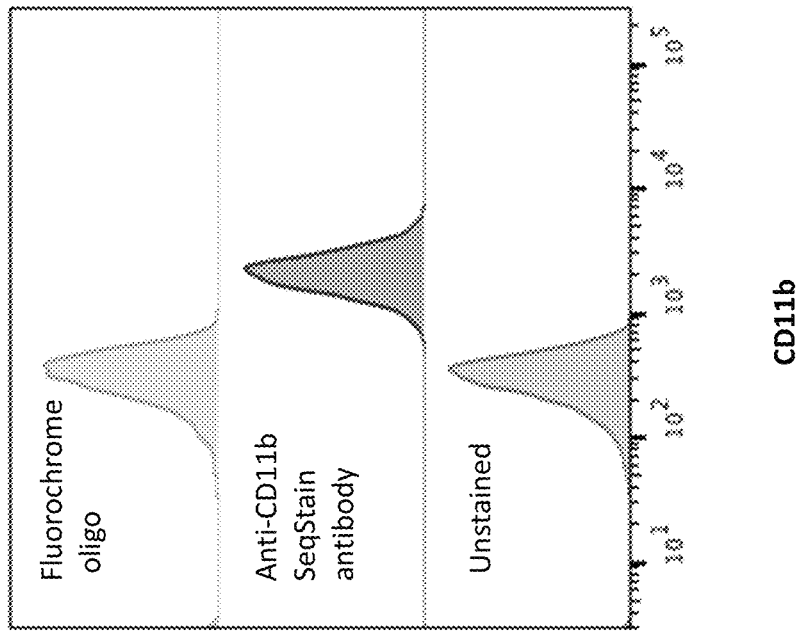
Figure 21C:
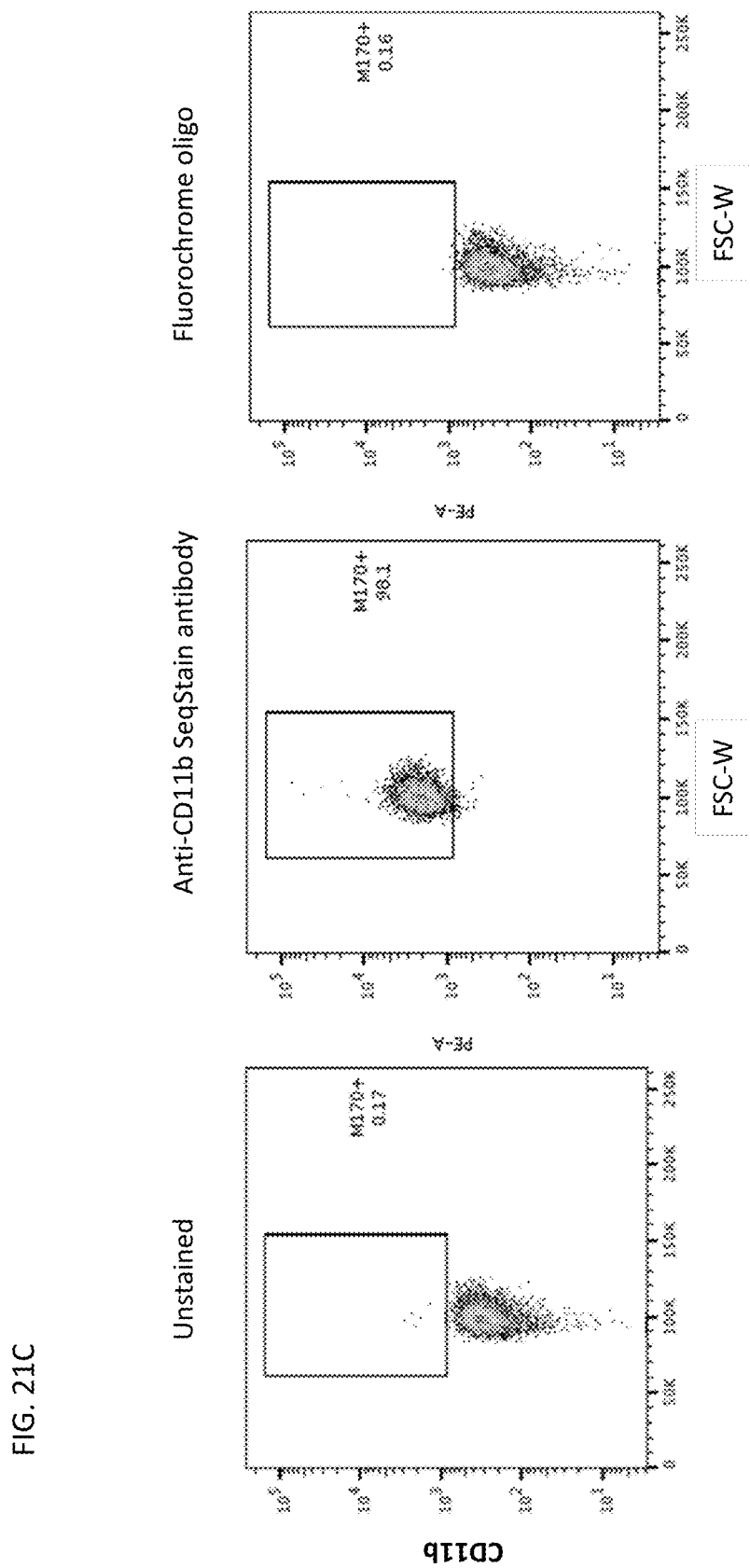

Flow cytometry validation of anti-CD45 and anti-CD11 SeqStaining is shown in FIG. 21A-21D. Anti-CD45 and anti-CD11b Abs were conjugated using maleimide-sulfhydryl chemistry to DNA oligo containing a restriction site and fluorochrome AF488 and AF594 respectively. RAW cells were stained by flow with anti-CD45 SeqStain Ab. For control, the DNA oligo complex without the antibody was used (FIG. 21A). Histogram of the staining is shown in FIG. 21B. Similarly staining for anti-CD11b SeqStainAb with AF594 is shown in FIG. 21C and FIG. 21D.

RAW cells were stained with two rounds of antibodies using the SeqStain method. Anti-CD45, anti-CD11b, anti-Acetylated tubulin and anti-Vinculin antibodies were conjugated using maleimide-sulfhydryl chemistry to DNA oligo containing a restriction site and fluorochrome AF488 or AF594. RAW cells were stained with anti-CD45 SeqStain Ab with AF488 and anti-CD11b antibody with AF594 in the first round and positive staining was viewed with fluorescence imaging. Destained using DNAseI was successful in removing staining and lack of stain in post destaining and post wash was observed. In round 2, the same sample was stained with anti-Acetylated tubulin SeqStain Ab with AF488 and anti-Vinculin SeqStain Ab with AF594 and positive staining was viewed with fluorescence imaging. Destained using DNAseI was successful in removing staining and lack of stain in post destaining and post wash was observed for the second round.

Comparison of SeqStain method with conventional method. Anti-Acetylated tubulin and anti-Ki-67 antibodies were conjugated using maleimide-sulfhydryl chemistry to DNA oligo containing a restriction site and fluorochrome AF488. HeLa cells were stained with either the SeqStain antibodies or the conventional method for acetylated tubulin or nuclear Ki-67 and similar fluorescence staining was observed with both methods.

Blocking with DNA solution alone helps reduce background. Anti-Acetylated tubulin SeqStain Ab with AF488 was used to stain RAW cells. Before staining blocking was either done in one-step containing 1% BSA and 3 nmoles/ml of blocking DNA mixture or it was done in two steps with 1% BSA in PBS for 45 minutes followed by blocking solution containing DNA mixture alone (100 ug/ml salmon sperm DNA and 3 nanomoles/ml blocking oligonucleotide in PBS with 0.5M NaCl) for 45 minutes followed by staining. Blocking solution containing oligonucleotide alone is better than blocking with a mixture of oligonucleotide and others agents, such as BSA, in the two step method.

Preparing antibody for SeqStain does not interfere with the antibody function. Anti-CD45 SeqStain Ab without the fluorochrome AF488 was used to stain RAW cells in two-step indirect immunofluorescence using anti-rat secondary AF488 antibody. No loss in staining was observed due to antibody modification for conjugation when compared to unmodified antibody.

Figure 22:
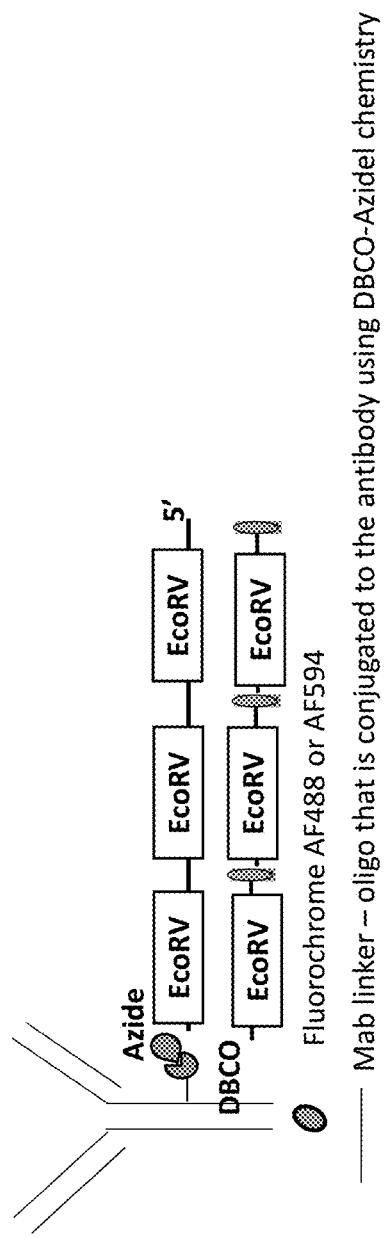

DBCO-Azide Click chemistry SeqStain antibody preparation. Anti-rat or anti-mouse Fabs were conjugated using DBCO-Azide Click chemistry to the mab linker DNA oligo as illustrated in FIG. 22A. Conjugation was verified by running the samples on a denaturing 4-12% SDS gel. Shift in the gel corresponding to the molecular weight of the mab linker showed successful conjugation.

Comparison of DBCO-Azide Click chemistry SeqStain method with conventional method. Anti-CD11b antibody was conjugated using DBCO-Azide Click chemistry to DNA oligo containing a restriction site and fluorochrome AF488. RAW cells were stained with either the SeqStain antibodies or the conventional method for CD11b. As a control, the DNA oligo complex without the antibody was used to stain the RAW cells. Similar fluorescence staining was observed with both methods.

K562 cells stable expressing CD11b stained with anti-CD11b SeqStain Ab and destained. Anti-CD11b Ab was conjugated using DBCO-Azide Click chemistry to DNA oligo containing a restriction site and fluorochrome AF488. K562 cells expressing CD11b were stained with anti-CD11b SeqStain Ab and positive staining was viewed with fluorescence imaging. Cells were destained using/restriction enzyme EcoRV. As a control, parent K562 cells were stained with anti-CD11b SeqStain Ab.

Figure 24A:
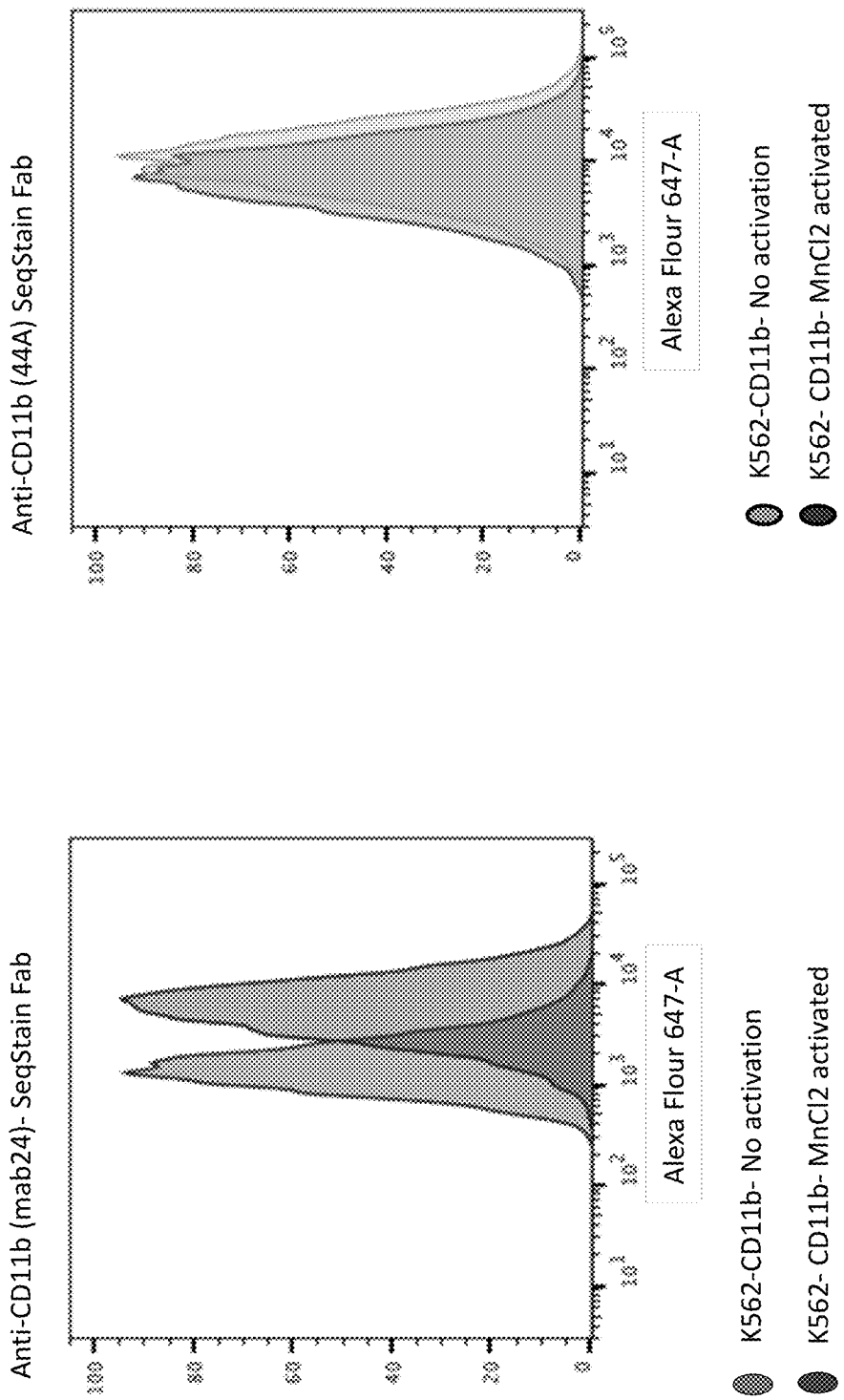

Flow staining of K562 cells expressing CD11b with or without activation. Anti-mouse Fab was conjugated using DBCO-Azide Click chemistry to DNA oligo containing a restriction site and fluorochrome AF647. Different clones of antibody against CD11b such as 44A, mab24 were used. Upon integrin activation by MnCl2, CD11b expresses the epitope for anti-CD11b (mab24) antibody. K562 cells expressing CD11b preferentially stain for anti-CD11b (mab24) antibody coupled to SeqStain Fab in 1:2 molar ratio when activated (FIG. 24A, Left Panel). Whereas, they stain well with anti-CD11b (44A) coupled to SeqStain Fab in 1:2 molar ratio regardless of the activation status (FIG. 24A, Right Panel). FIG. 24B shows staining of the antibodies coupled to SeqStain Fab compared to SeqStain Fab alone. FIG. 24B shows that SeqStain Fab when not coupled to the antibody shows no staining.

K562 cells expressing CD11b stained with three rounds of antibodies using the SeqStain method. Anti-mouse and anti-rat Fab were conjugated using DBCO-Azide Click chemistry to DNA oligo containing a restriction site and fluorochrome AF488 or AF594. Different clones of antibody against CD11b such as 44A, IB4 and M1/70 were used. Antibodies 44A and M170 were coupled with anti-mouse and anti-rat SeqStain Fab with AF488 respectively in 1:2 molar ratio. Whereas, IB4 antibody was coupled with anti-mouse SeqStain Fab with AF594 in 1:2 molar ratio. K562 cells expressing CD11b were stained with anti-CD11b (44A) antibody coupled to SeqStain Fab and then destained using EcoRV restriction enzyme (FIG. 25A). Two more rounds of staining and destaining was done using anti-CD11b (IB4) coupled to SeqStain Fab (FIG. 25B) and anti-CD11b (M1/70) coupled to SeqStain Fab (FIG. 25C). An advantage of using Fab in SeqStain is that the Fab can be coupled with antibody and used readily such that each antibody need not be prepared for SeqStain. In some embodiments, TCO-Tz Click Chemistry may be used.

RAW cells stained with anti-CD11b SeqStain Ab and destained. Biotinylated anti-CD11b Ab was conjugated to biotynylated DNA oligo containing a restriction site and fluorochrome AF488 using streptavidin in ratio of 1:1:3 of antibody: streptavidin: DNA oligo. RAW cells were stained with anti-CD11b SeqStain Ab and positive staining was viewed with fluorescence imaging. Cells were destained using restriction enzyme EcoRV.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

Remark et al., In-depth tissue profiling using multiplexed immunohistochemical consecutive staining on single slide, Science Immunology, 2016.

Carstens et al, Spatial computation of intratumoral T cells correlates with survival of patients with pancreatic cancer, Nature Comm., 2017.

Agasti et al., DNA barcoded labeling probes for highly multiplexed Exchange-PAINT imaging, Chem. Sci., 8, 3080, 2017.

Schnitzbauer et al., Super-resolution microscopy with DNA-PAINT, Nature Protocols, 12, 1198, 2017.

Collins et al., A branched DNA signal amplification assay for quantification of nucleic acid targets below 100 molecules/mL, Nucleic Acids Res., 25, 2979, 1997.

Sinnamon et al., RNA detection in situ with FISH-STICs, RNA, 20, 260, 2013.

Battich et al, Image-based transcriptomics in thousands of single human cells at single-molecule resolution, Nature Methods, 10, 1127, 2013.

Edman et al, Electric field directed nucleic acid hybridization on microchips, Nucleic Acids Research, 25, 4907, 1997.

Sosnowski et al, Rapid determination of single base mismatch mutations in DNA hybrids by direct electric field control, PNAS, 94, 1119, 1997.

Su et al., Kinetics of heterogeneous hybridization on indium tin oxide surfaces with and without an applied potential. Electrophoresis, No. 10, 1551-1557, May, 2002.

Sosnowski et al., Rapid determination of single base mismatch mutations in DNA hybrids by direct electric field control, PNAS, Vol. 94, 1119-1123, February, 1997.

Modi, S.; Swetha, M. G.; Goswami, D.; Gupta, G. D.; Mayor, S.; Krishnan, Y.* "A DNA nanomachine that maps spatial and temporal pH changes in living cells." Nature Nanotechnology, 2009, 4, 325-330. PMID: 19421220.

Saha, S., Prakash, V., Halder, S., Chakraborty, K., Krishnan, Y.* "A pH-insensitive DNA nanodevice quantifies chloride in organelles of living cells." Nature Nanotechnology, 2015, 10, 645-651. PMID: 26098226.

Chakraborty, K., Leung, K., Krishnan, Y.* "High lumenal chloride in the lysosome is critical for lysosome function." eLife, 2017, 6, e28862. PMID: 28742019.

Kwak, J. T., Hewitt, S. M., Kajdacsy-Balla, A. A., Sinha, S., & Bhargava, R. (2016). Automated prostate tissue referencing for cancer detection and diagnosis. BMC bioinformatics, 17(1), [227]. https://doi.org/10.1186/s12859-016-1086-6

Baker, M. J., Trevisan, J., Bassan, P., Bhargava, R., Butler, H. J., Dorling, K. M., Martin, F. L. (2014). Using Fourier transform IR spectroscopy to analyze biological materials. Nature protocols, 9(8), 1771-1791. https://doi.org/10.1038/nprot.2014.110

The invention claimed is:

1. A composition comprising:
an analyte detection agent comprising an analyte recognizing agent coupled to an oligonucleotide via a linker;
wherein the oligonucleotide is further coupled to a detection reagent;
wherein the oligonucleotide comprises one or more restriction sites;
wherein the detection reagent is enzymatically cleavable from the analyte recognizing agent at the one or more restriction sites; and
wherein the analyte detection agent comprises a branched DNA.

2. The composition of claim 1, wherein at least one oligonucleotide detection reagent comprises a fluorophore.

3. The composition of claim 1, wherein the oligonucleotide is single or double stranded.

4. The composition of claim 1, wherein the oligonucleotide comprises a fluorescent label.

5. The composition of claim 1, wherein the linker comprises a metal-based cross-linker, avidin, or streptavidin.

6. A method for analyzing a sample, the method comprising:
a. labeling a sample with one or more analyte detection agents, comprising an analyte recognizing agent coupled to an oligonucleotide via a linker, wherein:
the oligonucleotide is further coupled to a detection reagent and the oligonucleotide comprises one or more restriction sites;
b. detecting the signal generated by the analyte detection agent on the sample; and
c. removing the signal from each analyte detection agent through enzymatic cleavage using a restriction enzyme; and
wherein the at least one analyte detection agent comprises a branched DNA.

7. The method of claim 6, further comprising repeating steps a-c at least one additional time.

8. The method of claim 6, further comprising placing the sample on a planar surface.

9. The method of claim 8, further comprising adding a cross-linking agent to the planar surface.

10. The method of claim 6, comprising detecting at least 15 different signals from 15 different analytes.

* * * * *

SEQUENCE LISTING

<160> NUMBER OF SEQ ID NOS: 27

<210> SEQ ID NO 1
<211> LENGTH: 314
<212> TYPE: DNA
<213> ORGANISM: Artificial Sequence
<220> FEATURE:
<223> OTHER INFORMATION: Stem sequence

<400> SEQUENCE: 1
cggcatagca gcccgcatac tccacggccc tagggacaac gtccacggcc ctagggacaa      60
cgtccacggc cctagggaca acgtccacgg ccctagggac aacgtccacg gccctaggga     120
caacgtccac ggccctaggg acaacgtcca cggccctagg gacaacgtcc acggccctag     180
ggacaacgtc cacggcccta gggacaacgt ccacggccct agggacaacg tccacggccc     240
tagggacaac gtccacggcc ctagggacaa cgtccacggc cctagggaca cgtccacgg     300 ccctagggac aacg                                                      314

<210> SEQ ID NO 2
<211> LENGTH: 81
<212> TYPE: DNA
<213> ORGANISM: Artificial Sequence
<220> FEATURE:
<223> OTHER INFORMATION: branch oligonucleotide
<220> FEATURE:
<221> NAME/KEY: misc_feature
<222> LOCATION: (1)..(1)
<223> OTHER INFORMATION: n=5 me dC or amino-modified nucleotide
<220> FEATURE:
<221> NAME/KEY: misc_feature
<222> LOCATION: (4)..(4)
<223> OTHER INFORMATION: n=5 me dC or amino-modified nucleotide
<220> FEATURE:
<221> NAME/KEY: misc_feature
<222> LOCATION: (7)..(7)
<223> OTHER INFORMATION: n=5 me dC or amino-modified nucleotide
<220> FEATURE:
<221> NAME/KEY: misc_feature
<222> LOCATION: (10)..(10)
<223> OTHER INFORMATION: n=5 me dC or amino-modified nucleotide
<220> FEATURE:
<221> NAME/KEY: misc_feature
<222> LOCATION: (13)..(13)
<223> OTHER INFORMATION: n=5 me dC or amino-modified nucleotide
<220> FEATURE:
<221> NAME/KEY: misc_feature
<222> LOCATION: (16)..(16)
<223> OTHER INFORMATION: n=5 me dC or amino-modified nucleotide
<220> FEATURE:
<221> NAME/KEY: misc_feature
<222> LOCATION: (19)..(19)
<223> OTHER INFORMATION: n=5 me dC or amino-modified nucleotide
<220> FEATURE:
<221> NAME/KEY: misc_feature
<222> LOCATION: (22)..(22)
<223> OTHER INFORMATION: n=5 me dC or amino-modified nucleotide
<220> FEATURE:
<221> NAME/KEY: misc_feature
<222> LOCATION: (25)..(25)
<223> OTHER INFORMATION: n=5 me dC or amino-modified nucleotide
<220> FEATURE:
<221> NAME/KEY: misc_feature
<222> LOCATION: (28)..(28)
<223> OTHER INFORMATION: n=5 me dC or amino-modified nucleotide
<220> FEATURE:
<221> NAME/KEY: misc_feature
<222> LOCATION: (31)..(31)
<223> OTHER INFORMATION: n=5 me dC or amino-modified nucleotide
<220> FEATURE:
<221> NAME/KEY: misc_feature
<222> LOCATION: (34)..(34)
<223> OTHER INFORMATION: n=5 me dC or amino-modified nucleotide -continued

```
<220> FEATURE:
<221> NAME/KEY: misc_feature
<222> LOCATION: (37)..(37)
<223> OTHER INFORMATION: n=5 me dC or amino-modified nucleotide
<220> FEATURE:
<221> NAME/KEY: misc_feature
<222> LOCATION: (40)..(40)
<223> OTHER INFORMATION: n=5 me dC or amino-modified nucleotide
<220> FEATURE:
<221> NAME/KEY: misc_feature
<222> LOCATION: (43)..(43)
<223> OTHER INFORMATION: n=5 me dC or amino-modified nucleotide

<400> SEQUENCE: 2
nttnttnttn ttnttnttnt tnttnttntt nttnttnttn ttntttttt ttttttttt      60 cgttgtccct agggccgtgg a                                              81

<210> SEQ ID NO 3
<211> LENGTH: 81
<212> TYPE: DNA
<213> ORGANISM: Artificial Sequence
<220> FEATURE:
<223> OTHER INFORMATION: branch oligonucleotide
<220> FEATURE:
<221> NAME/KEY: misc_feature
<222> LOCATION: (1)..(1)
<223> OTHER INFORMATION: n=5 me dC or amino-modified nucleotide
<220> FEATURE:
<221> NAME/KEY: misc_feature
<222> LOCATION: (4)..(4)
<223> OTHER INFORMATION: n=5 me dC or amino-modified nucleotide
<220> FEATURE:
<221> NAME/KEY: misc_feature
<222> LOCATION: (7)..(7)
<223> OTHER INFORMATION: n=5 me dC or amino-modified nucleotide
<220> FEATURE:
<221> NAME/KEY: misc_feature
<222> LOCATION: (10)..(10)
<223> OTHER INFORMATION: n=5 me dC or amino-modified nucleotide
<220> FEATURE:
<221> NAME/KEY: misc_feature
<222> LOCATION: (13)..(13)
<223> OTHER INFORMATION: n=5 me dC or amino-modified nucleotide
<220> FEATURE:
<221> NAME/KEY: misc_feature
<222> LOCATION: (16)..(16)
<223> OTHER INFORMATION: n=5 me dC or amino-modified nucleotide
<220> FEATURE:
<221> NAME/KEY: misc_feature
<222> LOCATION: (19)..(19)
<223> OTHER INFORMATION: n=5 me dC or amino-modified nucleotide
<220> FEATURE:
<221> NAME/KEY: misc_feature
<222> LOCATION: (22)..(22)
<223> OTHER INFORMATION: n=5 me dC or amino-modified nucleotide
<220> FEATURE:
<221> NAME/KEY: misc_feature
<222> LOCATION: (25)..(25)
<223> OTHER INFORMATION: n=5 me dC or amino-modified nucleotide
<220> FEATURE:
<221> NAME/KEY: misc_feature
<222> LOCATION: (28)..(28)
<223> OTHER INFORMATION: n=5 me dC or amino-modified nucleotide
<220> FEATURE:
<221> NAME/KEY: misc_feature
<222> LOCATION: (31)..(31)
<223> OTHER INFORMATION: n=5 me dC or amino-modified nucleotide
<220> FEATURE:
<221> NAME/KEY: misc_feature
<222> LOCATION: (34)..(34)
<223> OTHER INFORMATION: n=5 me dC or amino-modified nucleotide
<220> FEATURE:
<221> NAME/KEY: misc_feature
<222> LOCATION: (37)..(37)
<223> OTHER INFORMATION: n=5 me dC or amino-modified nucleotide
<220> FEATURE:
```

```
<221> NAME/KEY: misc_feature
<222> LOCATION: (40)..(40)
<223> OTHER INFORMATION: n=5 me dC or amino-modified nucleotide
<220> FEATURE:
<221> NAME/KEY: misc_feature
<222> LOCATION: (43)..(43)
<223> OTHER INFORMATION: n=5 me dC or amino-modified nucleotide

<400> SEQUENCE: 3
nttnttnttn ttnttnttnt tnttnttntt nttnttnttn ttnttttttt tttttttttt    60
cgttgtcgct agagccgtgg a                                              81

<210> SEQ ID NO 4
<211> LENGTH: 48
<212> TYPE: DNA
<213> ORGANISM: Artificial Sequence
<220> FEATURE:
<223> OTHER INFORMATION: n site modification for SEQ ID 2 or 3

<400> SEQUENCE: 4
acgggatatc agattttacg ggatatcaga ttttacggga tatcagat                 48

<210> SEQ ID NO 5
<211> LENGTH: 48
<212> TYPE: DNA
<213> ORGANISM: Artificial Sequence
<220> FEATURE:
<223> OTHER INFORMATION: n modification for SEQ ID NO 2 or 3

<400> SEQUENCE: 5
acgggatatc agattttacg ggatatcaga ttttacggga tatcagat                 48

<210> SEQ ID NO 6
<211> LENGTH: 14
<212> TYPE: DNA
<213> ORGANISM: Artificial Sequence
<220> FEATURE:
<223> OTHER INFORMATION: labeld probe
<220> FEATURE:
<221> NAME/KEY: misc_feature
<222> LOCATION: (14)..(14)
<223> OTHER INFORMATION: 3' AF488

<400> SEQUENCE: 6
atctgatatc ccgt                                                      14

<210> SEQ ID NO 7
<211> LENGTH: 14
<212> TYPE: DNA
<213> ORGANISM: Artificial Sequence
<220> FEATURE:
<223> OTHER INFORMATION: labeled probe
<220> FEATURE:
<221> NAME/KEY: misc_feature
<222> LOCATION: (14)..(14)
<223> OTHER INFORMATION: 3' AF594

<400> SEQUENCE: 7
gtagcccggg tatg                                                      14

<210> SEQ ID NO 8
<211> LENGTH: 42
<212> TYPE: DNA
<213> ORGANISM: Artificial Sequence
<220> FEATURE:
<223> OTHER INFORMATION: linker oligonucleotide
```

<400> SEQUENCE: 8
acgggatatc agatacggga tatcagatac gggatatcag at                42

<210> SEQ ID NO 9
<211> LENGTH: 28
<212> TYPE: DNA
<213> ORGANISM: Artificial Sequence
<220> FEATURE:
<223> OTHER INFORMATION: linker oligonucleotide

<400> SEQUENCE: 9
acgggatatc agttacggga tatcagtt                                28

<210> SEQ ID NO 10
<211> LENGTH: 135
<212> TYPE: DNA
<213> ORGANISM: Artificial Sequence
<220> FEATURE:
<223> OTHER INFORMATION: clamp oligo1

<400> SEQUENCE: 10
aactgatatc ccgtaactga tatcccgttt ttttagcaa cagttatctc ggcaccattt    60
agcaacagtt atctcggcac catttagcaa cagttatctc ggcaccattt ttttgtatgc   120
cagaataatc atcgc                                                   135

<210> SEQ ID NO 11
<211> LENGTH: 100
<212> TYPE: DNA
<213> ORGANISM: Artificial Sequence
<220> FEATURE:
<223> OTHER INFORMATION: claimp oligo2

<400> SEQUENCE: 11
gtatgccaga ataatcatcg cttttttag caacagttat ctcggcacca tttagcaaca    60
gttatctcgg caccatttag caacagttat ctcggcacca                       100

<210> SEQ ID NO 12
<211> LENGTH: 93
<212> TYPE: DNA
<213> ORGANISM: Artificial Sequence
<220> FEATURE:
<223> OTHER INFORMATION: Stem oligo
<220> FEATURE:
<221> NAME/KEY: misc_feature
<222> LOCATION: (18)..(18)
<223> OTHER INFORMATION: n=5-amino modified thymidine or 5-hydroxy
      modified thymidine
<220> FEATURE:
<221> NAME/KEY: misc_feature
<222> LOCATION: (21)..(21)
<223> OTHER INFORMATION: n=5-amino modified thymidine or 5-hydroxy
      modified thymidine
<220> FEATURE:
<221> NAME/KEY: misc_feature
<222> LOCATION: (24)..(24)
<223> OTHER INFORMATION: n=5-amino modified thymidine or 5-hydroxy
      modified thymidine
<220> FEATURE:
<221> NAME/KEY: misc_feature
<222> LOCATION: (27)..(27)
<223> OTHER INFORMATION: n=5-amino modified thymidine or 5-hydroxy
      modified thymidine
<220> FEATURE:
<221> NAME/KEY: misc_feature
<222> LOCATION: (30)..(30)
<223> OTHER INFORMATION: n=5-amino modified thymidine or 5-hydroxy
      modified thymidine

```
<220> FEATURE:
<221> NAME/KEY: misc_feature
<222> LOCATION: (33)..(33)
<223> OTHER INFORMATION: n=5-amino modified thymidine or 5-hydroxy
      modified thymidine
<220> FEATURE:
<221> NAME/KEY: misc_feature
<222> LOCATION: (36)..(36)
<223> OTHER INFORMATION: n=5-amino modified thymidine or 5-hydroxy
      modified thymidine
<220> FEATURE:
<221> NAME/KEY: misc_feature
<222> LOCATION: (39)..(39)
<223> OTHER INFORMATION: n=5-amino modified thymidine or 5-hydroxy
      modified thymidine
<220> FEATURE:
<221> NAME/KEY: misc_feature
<222> LOCATION: (42)..(42)
<223> OTHER INFORMATION: n=5-amino modified thymidine or 5-hydroxy
      modified thymidine
<220> FEATURE:
<221> NAME/KEY: misc_feature
<222> LOCATION: (45)..(45)
<223> OTHER INFORMATION: n=5-amino modified thymidine or 5-hydroxy
      modified thymidine
<220> FEATURE:
<221> NAME/KEY: misc_feature
<222> LOCATION: (48)..(48)
<223> OTHER INFORMATION: n=5-amino modified thymidine or 5-hydroxy
      modified thymidine
<220> FEATURE:
<221> NAME/KEY: misc_feature
<222> LOCATION: (51)..(51)
<223> OTHER INFORMATION: n=5-amino modified thymidine or 5-hydroxy
      modified thymidine
<220> FEATURE:
<221> NAME/KEY: misc_feature
<222> LOCATION: (54)..(54)
<223> OTHER INFORMATION: n=5-amino modified thymidine or 5-hydroxy
      modified thymidine
<220> FEATURE:
<221> NAME/KEY: misc_feature
<222> LOCATION: (57)..(57)
<223> OTHER INFORMATION: n=5-amino modified thymidine or 5-hydroxy
      modified thymidine
<220> FEATURE:
<221> NAME/KEY: misc_feature
<222> LOCATION: (60)..(60)
<223> OTHER INFORMATION: n=5-amino modified thymidine or 5-hydroxy
      modified thymidine
<220> FEATURE:
<221> NAME/KEY: misc_feature
<222> LOCATION: (63)..(63)
<223> OTHER INFORMATION: n=5-amino modified thymidine or 5-hydroxy
      modified thymidine

<400> SEQUENCE: 12
ttgacagctg ccggattntt nttnttnttn ttnttnttnt tnttnttntt nttnttnttn      60
ttnttttttt ttggtgccga gataactgtt gct                                  93

<210> SEQ ID NO 13
<211> LENGTH: 63
<212> TYPE: DNA
<213> ORGANISM: Artificial Sequence
<220> FEATURE:
<223> OTHER INFORMATION: anchor oligo

<400> SEQUENCE: 13
tttttgacag ctgccggatt ttttttttgac agctgccgga tttttttttg acagctgccg    60
gat                                                                   63

<210> SEQ ID NO 14
<211> LENGTH: 15
```

```
<212> TYPE: DNA
<213> ORGANISM: Artificial Sequence
<220> FEATURE:
<223> OTHER INFORMATION: labeled oligo probe
<220> FEATURE:
<221> NAME/KEY: misc_feature
<222> LOCATION: (1)..(1)
<223> OTHER INFORMATION: 5' label

<400> SEQUENCE: 14
tccggcagct gtcaa                                                      15

<210> SEQ ID NO 15
<211> LENGTH: 15
<212> TYPE: DNA
<213> ORGANISM: Artificial Sequence
<220> FEATURE:
<223> OTHER INFORMATION: labeled oligo probe
<220> FEATURE:
<221> NAME/KEY: misc_feature
<222> LOCATION: (1)..(1)
<223> OTHER INFORMATION: 5' AF488

<400> SEQUENCE: 15
tccggcagct gtcaa                                                      15

<210> SEQ ID NO 16
<211> LENGTH: 15
<212> TYPE: DNA
<213> ORGANISM: Artificial Sequence
<220> FEATURE:
<223> OTHER INFORMATION: labeled probe
<220> FEATURE:
<221> NAME/KEY: misc_feature
<222> LOCATION: (1)..(1)
<223> OTHER INFORMATION: 5' biotin

<400> SEQUENCE: 16
tccggcagct gtcaa                                                      15

<210> SEQ ID NO 17
<211> LENGTH: 15
<212> TYPE: DNA
<213> ORGANISM: Artificial Sequence
<220> FEATURE:
<223> OTHER INFORMATION: labeled oligo probe
<220> FEATURE:
<221> NAME/KEY: misc_feature
<222> LOCATION: (1)..(1)
<223> OTHER INFORMATION: 5' AF594

<400> SEQUENCE: 17
tccggcagct gtcaa                                                      15

<210> SEQ ID NO 18
<211> LENGTH: 48
<212> TYPE: DNA
<213> ORGANISM: Artificial Sequence
<220> FEATURE:
<223> OTHER INFORMATION: hinge oligo

<400> SEQUENCE: 18
gcgttgatta ttctggcata caaaaaagcg ttgattattc tggcatac                  48

<210> SEQ ID NO 19
<211> LENGTH: 19
<212> TYPE: DNA
<213> ORGANISM: Artificial Sequence
<220> FEATURE:
```

```
<223> OTHER INFORMATION: Mab linker

<400> SEQUENCE: 19
ccgtagcaga tatcacagc                                                  19

<210> SEQ ID NO 20
<211> LENGTH: 90
<212> TYPE: DNA
<213> ORGANISM: Artificial Sequence
<220> FEATURE:
<223> OTHER INFORMATION: docking oligonucleotide

<400> SEQUENCE: 20
ttgacagctg ccggattgac agctgccgga ttgacagctg ccggattgac agctgccgga    60
ttgacagctg ccggagctgt gatatctgct                                     90

<210> SEQ ID NO 21
<211> LENGTH: 19
<212> TYPE: DNA
<213> ORGANISM: Artificial Sequence
<220> FEATURE:
<223> OTHER INFORMATION: Mab linker

<400> SEQUENCE: 21
ccgtagcacc cgggacagc                                                  19

<210> SEQ ID NO 22
<211> LENGTH: 90
<212> TYPE: DNA
<213> ORGANISM: Artificial Sequence
<220> FEATURE:
<223> OTHER INFORMATION: Docking oligonucleotide

<400> SEQUENCE: 22
ttgacagctg ccggattgac agctgccgga ttgacagctg ccggattgac agctgccgga    60
ttgacagctg ccggagctgt cccgggtgct                                     90

<210> SEQ ID NO 23
<211> LENGTH: 15
<212> TYPE: DNA
<213> ORGANISM: Artificial Sequence
<220> FEATURE:
<223> OTHER INFORMATION: Fluor Oligo
<220> FEATURE:
<221> NAME/KEY: misc_feature
<222> LOCATION: (15)..(15)
<223> OTHER INFORMATION: 3' AF488

<400> SEQUENCE: 23
tccggcagct gtcaa                                                      15

<210> SEQ ID NO 24
<211> LENGTH: 15
<212> TYPE: DNA
<213> ORGANISM: Artificial Sequence
<220> FEATURE:
<223> OTHER INFORMATION: Fluoro oligo
<220> FEATURE:
<221> NAME/KEY: misc_feature
<222> LOCATION: (15)..(15)
<223> OTHER INFORMATION: 3' AF594

<400> SEQUENCE: 24
tccggcagct gtcaa                                                      15
```

```
<210> SEQ ID NO 25
<211> LENGTH: 42
<212> TYPE: DNA
<213> ORGANISM: Artificial Sequence
<220> FEATURE:
<223> OTHER INFORMATION: Mab linker

<400> SEQUENCE: 25
acgggatatc agatacggga tatcagatac gggatatcag at                           42

<210> SEQ ID NO 26
<211> LENGTH: 14
<212> TYPE: DNA
<213> ORGANISM: Artificial Sequence
<220> FEATURE:
<223> OTHER INFORMATION: Fluor oligo
<220> FEATURE:
<221> NAME/KEY: misc_feature
<222> LOCATION: (14)..(14)
<223> OTHER INFORMATION: 3' AF488

<400> SEQUENCE: 26
atctgatatc ccgt                                                         14

<210> SEQ ID NO 27
<211> LENGTH: 14
<212> TYPE: DNA
<213> ORGANISM: Artificial Sequence
<220> FEATURE:
<223> OTHER INFORMATION: Fluor oligo
<220> FEATURE:
<221> NAME/KEY: misc_feature
<222> LOCATION: (14)..(14)
<223> OTHER INFORMATION: 3' AF594

<400> SEQUENCE: 27
atctgatatc ccgt                                                         14
```